(12) United States Patent
Raine et al.

(10) Patent No.: US 11,198,865 B2
(45) Date of Patent: Dec. 14, 2021

(54) SPLINTED LIGATION ADAPTER TAGGING

(71) Applicants: Amanda Raine, Järlåsa (SE); Jessica Nordlund, Uppsala (SE)

(72) Inventors: Amanda Raine, Järlåsa (SE); Jessica Nordlund, Uppsala (SE)

(*) Notice: Subject to any disclaimer, the term of this patent is extended or adjusted under 35 U.S.C. 154(b) by 107 days.

(21) Appl. No.: 16/178,647

(22) Filed: Nov. 2, 2018

(65) Prior Publication Data

US 2019/0194649 A1 Jun. 27, 2019

Related U.S. Application Data

(60) Provisional application No. 62/580,465, filed on Nov. 2, 2017.

(51) Int. Cl.
| | |
|---|---|
| *C12P 19/34* | (2006.01) |
| *C12N 15/10* | (2006.01) |
| *C12Q 1/686* | (2018.01) |

(52) U.S. Cl.
CPC ......... *C12N 15/1065* (2013.01); *C12Q 1/686* (2013.01)

(58) Field of Classification Search
USPC ............ 435/6.1, 6.11, 6.12, 91.1, 91.2, 183; 436/94, 501; 536/23.1, 24.3, 24.33, 25.3
See application file for complete search history.

(56) References Cited

PUBLICATIONS

Moore et al., Joining of RNAs by Splinted Ligation. Methods in Enzymology, 317, 109-123, 2000.*
Raine et al., "SPlinted Ligation Adapter Tagging (SPLAT), a Novel Library Preparation Method for Whole Genome Bisulphite Sequencing," Nucleic Acids Research, vol. 45, No. 6, (Nov. 29, 2017), p. e36.
Jones et al., "Functions of DNA Methylation: Islands, Start Sites, Gene Bodies and Beyond," Nat. Rev. Genet., 13, (2012) pp. 484-492.
Portela et al., "Epigenetic Modifications and Human Disease," Nat. Biotechnol., 28, (2010), pp. 1057-1068.
Lister et al., "Highly Integrated Single-Base Resolution Maps of the Epigenome in *Arabidopsis*," Cell, 133, (2008), pp. 523-536.
Cokus et al., "Shotgun Bisulphite Sequencing of the *Arabidopsis* Genome Reveals DNA Methylation Patterning," Nature, 452, (2008), pp. 215-219.
Bibikova et al. High Density DNA Methylation Array with Single CpG Site Resolution, Genomics, 98, (2011), pp. 288-295.

(Continued)

*Primary Examiner* — Frank W Lu
(74) *Attorney, Agent, or Firm* — Porter Wright Morris & Arthur LLP

(57) ABSTRACT

A method is provided comprising the following steps: (a) treating a nucleic acid with bisulfite to convert non-methylated cytosines in the nucleic acid into uracils while leaving methylated cytosines unchanged to form a treated nucleic acid strand that is part of two joined nucleic acid strands; (b) ligating a first adapter to a 3' end of the treated nucleic acid strand, the first adapter having a first protruding random sequence that least 3 bases long and that acts as a splint for the two joined nucleic acid strands; (c) ligating a second adapter to a 5' end of the once adapter ligated nucleic acid strand, the second adapter having a second protruding random sequence at least 3 bases long and that acts as a splint for the two joined nucleic acid strands; and (d) performing PCR amplification on the twice ligated nucleic acid strand.

6 Claims, 31 Drawing Sheets

Specification includes a Sequence Listing.

(56) References Cited

PUBLICATIONS

Moran et al., "Validation of a DNA Methylation Microarray for 850,000 CpG Sites of the Human Genome Enriched in Enhancer Sequences," Epigenomics, 8, (2015), pp. 389-399.

Sandoval et al., "Validation of a DNA Methylation Microarray for 450,000 CpG Sites in the Human Genome," Epigenetics, 6, (2011), pp. 692-702.

Gu et al., "Preparation of Reduced Representation Bisulfite Sequencing Libraries for Genome-Scale DNA Methylation Profiling," Nature Protocols, 6, (2011), pp. 468-481.

Meissner et al., "Genome-Scale DNA Methylation Maps of Pluripotent and Differentiated Cells," Nature, 454, (2008), pp. 766-770.

Court et al., "Genome-Wide Parent-of-Origin DNA Methylation Analysis Reveals the Intricacies of Human Imprinting and Suggests a Germline Methylation-Independent Mechanism of Establishment," Genome Res., 24, 2014), pp. 554-569.

Uribe-Lewis et al.,"Molecular Mechanisms of Genomic Imprinting and Clinical Implications for Cancer," Expert Rev. Mol. Med., 13, (2011), p. e2.

Benjamini et al., Summarizing and Correcting the GC Content Bias in High-Throughput Sequencing< Nucleic Acids Res., 40, (2012), p. e72.

Aird et al., Analyzing and Minimizing PCR Amplification Pias in Illumina Sequencing Libraries. Genome Biol., 12, (2011), p. R18.

Frommer et al., "A Genomic Sequencing Protocol that Yields a Positive Display of 5-Methylcytosine Residues in Individual DNA Strands," Proc. Natl. Acad. Sci. U.S.A., 89, (1992), pp. 1827-1831.

Gansauge et al. Nature Protocols 8, (2013), pp. 737-748.

Smallwood et al., "Single-Cell Genome-Wide Bisulfite Sequencing for Assessing Epigenetic Heterogeneity," Nat. Methods, 11, (2014), pp. 817-820.

Rosenfeld et al., An Effect Human Leukaemic Cell Line: Reh. Eur. J. Cancer, 13, (1977), pp. 377-379.

Krueger et al., Bioinformatics (Oxford, England). vol. 27, (2011), pp. 1571-1572.

Garcia-Alcalde et al., "Qualimap: Evaluating Next-Generation Sequencing Alignment Data," Bioinformatics (Oxford, England), 28, (2012), pp. 2678-2679.

Quinlan, "BEDTools: the Swiss-Army Tool for Genome Feature Analysis," Curr. Protoc. Bioinformatics, 47, (2012), p. doi:10.1002/0471250953.bi1112s47.

Burger et al., "Identification of Active Regulatory Regions from DNA Methylation Data," Nucleic Acids Res., 41, (2012), p. e155.

Lawrence et al., "Software for Computing and Annotating Genomic Ranges," PLoS Comput. Biol., 9, (2013), p. e1003118.

Nordlund et al., "Genome-Wide Signatures of Differential DNA Methylation in Pediatric Acute Lymphoblastic Leukemia," Genome Biol., 14, (2013), p. r105.

Smith et al., "High-Throughput Bisulfite Sequencing in Mammalian Genomes," Methods (San Diego, Calif.), 48, (2009), pp. 226-232.

Boyle et al., "Gel-Free Multiplexed Reduced Representation Bisulfite Sequencing for Large-Scale DNA Methylation Profiling," Genome Biol., 13, (2012), p. R92.

Deng et al., "Targeted Bisulfite Sequencing Reveals Changes in DNA Methylation Associated with Nuclear Reprogramming," Nat. Biotechnol., 27, (2009), pp. 353-360.

Diep et al.,"Library-Free Methylation Sequencing with Bisulfite Padlock Probes," Nat. Methods, 9, (2012), pp. 270-272.

Ivanov et al., "In-Solution Hybrid Capture of Bisulfite-Converted DNA for Targeted Bisulfite Sequencing of 174 ADME Genes," Nucleic Acids Res., 41, (2013), p. e72.

Lee et al., "Targeted Bisulfite Sequencing by Solution Hybrid Selection and Massively Parallel Sequencing," Nucleic Acids Res., 39, (2011), p. e127.

Allum et al., "Characterization of Functional Methylomes by Next-Generation Capture Sequencing Identifies Novel Disease-Associated Variants," Nat. Commun., 6, (2015), p. 7211.

Adey et al., "Ultra-Low-Input, Tagmentation-Based Whole-Genome Bisulfite Sequencing," Genome Res., 22, (2012), pp. 1139-1143.

Miura et al., "Amplification-Free Whole-Genome Bisulfite Sequencing by Post-Bisulfite Adapter Tagging," Nucleic Acids Res. 40, (2012), p. e136.

Miura et al., "Highly Sensitive Targeted Methylome Sequencing by Post-Bisulfite Adapter Tagging," DNA Res., 22, (2015), pp. 13-18.

* cited by examiner

Table 1

Sequence metrics for whole genome bisulfite libraries

| Method & DNA quantity | Cell line | PCR cycles | Mapping efficiency (%)[a] | | Aligned read pairs (M)[a] | | PCR duplicates (%) |
|---|---|---|---|---|---|---|---|
| TruSeq/ | NA10860 | 9 | 76 | 77 | 133 | 126 | 13–17 |
| 100 ng | REH | 9 | 78 | 78 | 133 | 141 | 12–15 |
| Accel-NGS/ | NA10860 | 4 | 83 | 82 | 129 | 131 | 1–2 |
| 100 ng | REH | 4 | 82 | 82 | 100 | 115 | 1–2 |
| SPLAT/ | NA10860 | 4 | 70 | 70 | 92 | 128 | 1–2 |
| 100 ng | REH | 4 | 83 | 77 | 136 | 176 | 1–2 |
| NEBNextUltra/ | NA10860 | 6 | 75 | 75 | 131 | 102 | 1–2 |
| 1000 ng | REH | 6 | 79 | 79 | 129 | 125 | 1–2 |

[a] for each individual sequenced library (technical replicates).

*FIG. 8*

Table 2

Read coverage and correlation of methylation between SPLAT and high coverage reference data

| WGBS data | Average read coverage | Average CpG coverage | | Correlation of methylation (Pearsons R) |
|---|---|---|---|---|
| NA10860 SPLAT | 16× | 13× | NA10860; SPLAT versus reference | 0.94 |
| NA10860 high coverage reference | 49× | 36× | | |
| REH SPLAT | 22× | 17× | REH; SPLAT versus reference | 0.97 |
| REH high coverage reference | 49× | 36× | | |

*FIG. 9*

Table 3

Correlation of DNA methylation levels of CpG sites with binned coverage in SPLAT with the high coverage reference libraries.

| Cell line | Coverage in SPLAT library | N CpGs | Pearson's R[a] |
|---|---|---|---|
| NA10860 | 0-4x | 886189 | 0.907 |
| | 5-9x | 4471785 | 0.928 |
| | 10-14x | 8561265 | 0.937 |
| | 15-20x | 7860513 | 0.948 |
| | 21-25x | 1926079 | 0.956 |
| REH | 0-4x | 448523 | 0.953 |
| | 5-9x | 2209689 | 0.966 |
| | 10-14x | 5172832 | 0.964 |
| | 15-20x | 8643144 | 0.966 |
| | 21-25x | 4765508 | 0.972 |

[a] CpG site coverage in the reference library is >20x.

FIG. 11

Table 4

| Library[a] | # reads | Gb | mapped reads (unique)[b] | mapped Gb data (unique) | mean coverage | median insert size | mean insert size | % of raw data retained[c] |
|---|---|---|---|---|---|---|---|---|
| NA10860 TruSeq | 684.6 M | 84.8 | 438.4 M | 46.5 | 15.1x | 139 | 159 | 55 |
| REH TruSeq | 710.4 M | 88.0 | 474.4 M | 51.7 | 16.7x | 140 | 157 | 58 |
| NA10860 SPLAT | 637.0 M | 79.0 | 436.5 M | 51.2 | 16.6x | 186 | 198 | 65 |
| REH SPLAT | 728.8 M | 90.1 | 571.0 M | 68.1 | 22.0x | 180 | 193 | 76 |
| NA10860 Accel | 637.2 M | 79.0 | 514.9 M | 52.2 | 16.9x | 157 | 173 | 66 |
| REH Accel | 532.8 M | 66.2 | 426.4 M | 43.2 | 14.0x | 152 | 168 | 65 |
| NA10860 NEB | 629.2 M | 78.0 | 462.3 M | 53.6 | 17.3x | 177 | 192 | 69 |
| REH NEB | 646.0 M | 80.2 | 501.3 M | 57.3 | 18.5x | 167 | 183 | 71 |

[a] data from two technical replicates combined. [b] PCR duplicates removed. [c] After pre-processing, alignment and deduplication.

FIG. 14

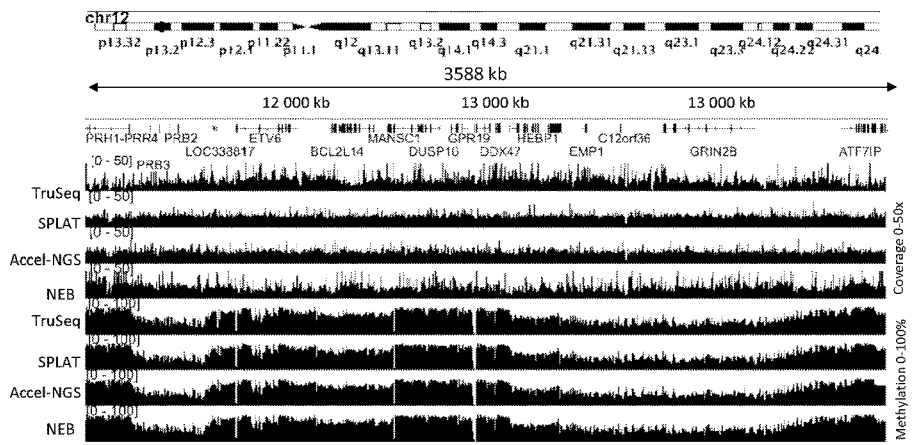
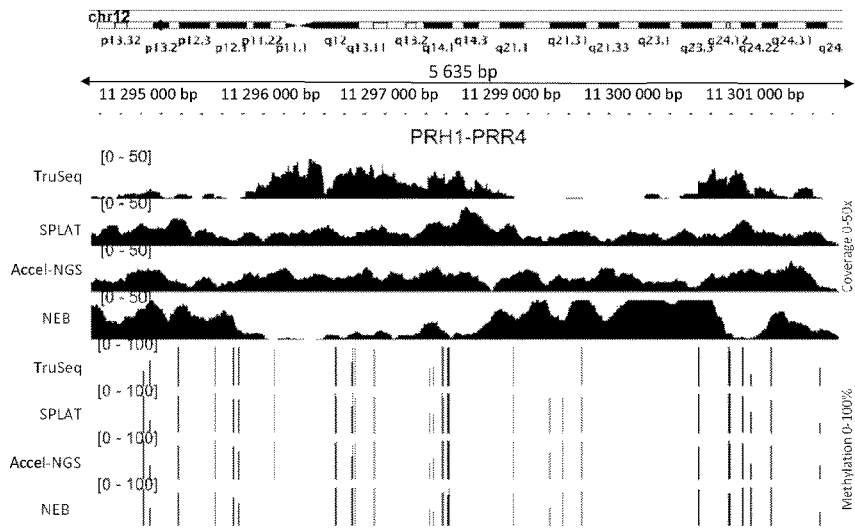
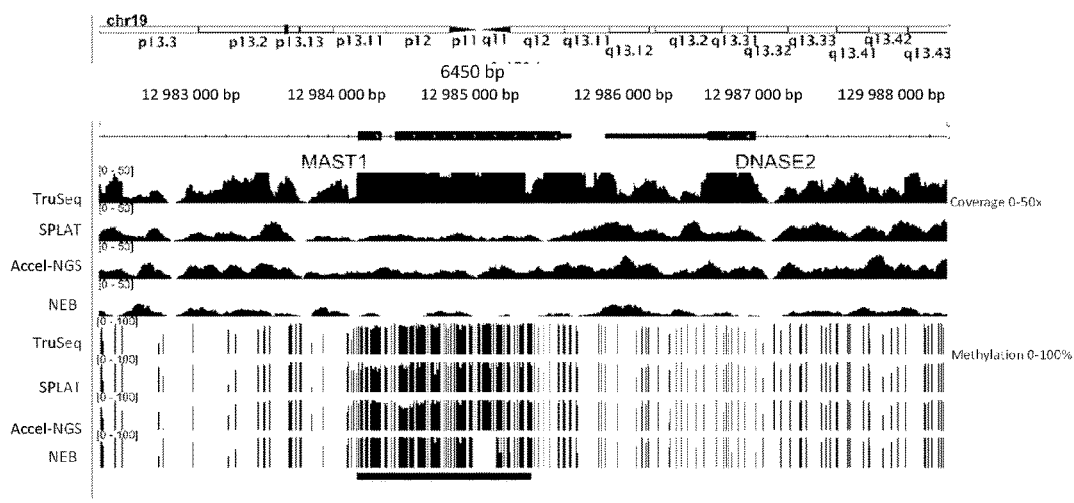
*FIG. 16*

Table 5

| Library | Total # cytosines analysed | Cytosines methylated in CpG context[a] | Cytosines methylated in CHG context | Cytosines methylated in CHH context[b] |
|---|---|---|---|---|
| NA10860-TruSeq | 6261577653 | 59.3% | 0.8% | 0.7% |
| REH-TruSeq | 6842638048 | 80.3% | 0.9% | 0.8% |
| NA10860-Accel | 7821734884 | 57.4% | 0.4% | 0.3% |
| REH-Accel | 6425286945 | 82.6% | 0.4% | 0.4% |
| NA10860-SPLAT | 7712370882 | 57.2% | 0.4% | 0.4% |
| REH-SPLAT | 3992058618 | 81.8% | 0.4% | 0.4% |
| NA10860-NEBNextUltra | 6460945191 | 57.4% | 0.4% | 0.4% |
| REH-NEBNextUltra | 7029883811 | 82.6% | 0.9% | 1.0% |

[a] Percentage of methylated cytosines in a CpG context across all sequenced reads.
[b] Methylation in non CpG context was lower than 1 %, indicating high bisulfite conversion rates (≥99%).

FIG. 18

Table 6

| Library[b] | N CpG sites | Average methylation (%) |
|---|---|---|
| NA10860-TruSeq | 435 | 46.5 |
| REH-TruSeq | 435 | 65.6 |
| NA10860-TruSeq2[a] | 435 | 27.5 |
| NA10860-SPLAT | 435 | 0.31 |
| REH-SPLAT | 435 | 0.32 |
| NA10860-Accel | 435 | 0.31 |
| REH-Accel | 435 | 0.34 |
| NA10860-NEBNextUltra | 435 | 0.39 |
| REH-NEBNextUltra | 435 | 0.9 |

[a]data from a third TruSeq DNA Methylation technical replicate. [b]Methylation levels were low at mitochondrial CpG sites in the SPLAT, Accel-NGS Methyl-Seq and NEBNextUltra libraries which is consistent with a high bisulfite conversion rate. For the TruSeq DNA Methylation libraries, the methylation level at mitochondrial CpG sites was high. This observation was in contrast to the low methylation levels observed at cytosines in non CpG context in the autosomes.

FIG. 19

Table 7

| Library type | Cell line | % Usable reads for "within read" analysis[a] | % of reads with concordant "within read" methylation levels | % of reads with discordant "within read" methylation levels |
|---|---|---|---|---|
| SPLAT | NA10680 | 26 | 60 | 40 |
| Accel-NGS | NA10680 | 22 | 63 | 37 |
| TruSeq DNA Methylation | NA10680 | 35 | 60 | 40 |
| NebNextUltra | NA10680 | 17 | 60 | 40 |
| SPLAT | REH | 26 | 78 | 22 |
| Accel-NGS | REH | 23 | 80 | 20 |
| TruSeq DNA Methylation | REH | 36 | 77 | 23 |
| NebNextUltra | REH | 18 | 76 | 24 |

[a] usable read are defined as reads containing 2 or more CpG sites.

FIG. 20

Table 8

| Technical replicates*<br>NA10860 | CpG sites ≥5x<br>Pearson's R | CpG sites ≥10x<br>Pearson's R |
|---|---|---|
| TruSeq DNA methylation | 0.89 | 0.93 |
| AccelNGS | 0.86 | 0.90 |
| SPLAT | 0.87 | 0.90 |
| NEBNextUltra | 0.84 | 0.91 |
| Technical replicates*<br>REH | CpG sites ≥5x<br>Pearson' R | CpG sites ≥10x<br>Pearson' R |
| TruSeq DNA methylation | 0.94 | 0.96 |
| AccelNGS | 0.91 | 0.94 |
| SPLAT | 0.92 | 0.95 |
| NEBNextUltra | 0.87 | 0.91 |

*The average genome coverage in the technical replicates was 7-11x.

FIG. 22

Table 9

| Method | Cell line | PCR cycles | Mapping efficiency (%) | Aligned Read pairs | PCR duplicates |
|---|---|---|---|---|---|
| RRBS | REH | 11 | 75 | 10 M | NA |
| | NA10860 | 11 | 70 | 9 M | NA |
| SureSelect Methyl-Seq | REH | 8 | 86 | 51 M | 32 % |
| | NA10860 | 8 | 87 | 104 M | 58 % |

FIG. 23

Table 10

| Library | # LMRs | # UMRs | # read pairs analysed |
|---|---|---|---|
| NA10860 TruSeq DNA Methylation | 27475 | 17284 | 219 M |
| NA10860 SPLAT | 28438 | 16681 | 218 M |
| NA10860 Accel-NGS | 27420 | 16609 | 218 M |
| NA10860 NEBNextUltra | 17632 | 13240 | 219 M |
| REH TruSeq DNA Methylation | 51828 | 14227 | 211 M |
| REH SPLAT | 58435 | 14581 | 213 M |
| REH Accel-NGS | 59023 | 14576 | 213 M |
| REH NEBNextUltra | 29519 | 13012 | 216 M |

Low methylated region (LMR); Un-methylated region (UMR)

*FIG. 27*

Table 11

| Library | N analyzed read pairs | N CpG sites covered by zero reads | N CpG sites covered by ≥5 reads | N CpG sites covered by ≥10 reads |
|---|---|---|---|---|
| NA10860 TruSeq | 219 M | 1.04 M | 23.1 M (82%) | 17.5 M (62%) |
| REH TruSeq | 211 M | 0.92 M | 23.2 M (84%) | 17.0 M (62%) |
| NA10860 SPLAT | 218 M | 0.49 M | 25.5 M (90%) | 19.5 M (69%) |
| REH SPLAT | 213 M | 0.55 M | 24.9 M (89%) | 18.2 M (65%) |
| NA10860 Accel-NGS | 218 M | 0.53 M | 24.9 M (89%) | 16.5 M (58%) |
| REH Accel-NGS | 213 M | 0.52 M | 24.5 M (88%) | 16.1 M (58%) |
| NA10860 NEBNextUltra | 219 M | 1.59 M | 17.5 M (62%) | 9.2 M (33%) |
| REH NEBNextUltra | 216 M | 1.01 M | 18.9 M (67%) | 9.3 M (34%) |
| NA10860 RRBS | 20 M | n.d | 2.9 M | 2.2 M |
| REH RRBS | 10 M | n.d | 1.0 M | 0.2 M |
| NA10860 SureSelect | 44 M | n.d | 3.9 M | 3.2 M |
| REH SureSelect | 35 M | n.d | 3.6 M | 2.9 M |

M = million.

*FIG. 28*

Table 12

| Library | Genomic feature | CpGs covered by 0-2 reads |
|---|---|---|
| NA10860 NEBNextUltra | all | 6041191 |
| | repeat | 2609150 |
| | intergenic | 2135952 |
| | intron | 2949400 |
| | exon | 1232224 |
| | promoter | 2589475 |
| | CpGIsland | 1527940 |
| REH NEBNextUltra | all | 4676624 |
| | repeat | 2078228 |
| | intergenic | 1568098 |
| | intron | 2229998 |
| | exon | 887301 |
| | promoter | 1918538 |
| | CpGIsland | 1100174 |

*FIG. 29*

Table 13

| | TruSeq DNA methylation | SPLAT | Accel-NGS Methyl-Seq | NEBNextUltra |
|---|---|---|---|---|
| Input DNA quantity | 50–100 ng | ≤100 ng | ≤100 ng | ~1000 ng |
| Number of PCR cycles | 9 | 4 (100 ng input) | 4 (100 ng input) | 6 |
| Amount of PCR duplicates | High | Low | Low | Low |
| Genome coverage | GC biased | Relatively uniform | Relatively uniform | AT biased |
| Advantages | Excellent coverage of CpG dense regions | High total CpG site coverage | High total CpG site coverage | – |
| | Methylation highly concordant with other methods | Methylation highly concordant with other methods | Methylation highly concordant with other methods | |
| | | Very low library prep cost | | |
| Disadvantages | High proportion of data removed in pre-processing steps | Coverage in CpG dense regions is lower than the average coverage | Coverage in CpG dense regions is lower than the average coverage | Overall low coverage of CpG sites, particularly in CpG dense regions |
| | | | Sequence tag removal is required | |

FIG. 31

SPLINTED LIGATION ADAPTER TAGGING

CROSS-REFERENCE TO RELATED APPLICATIONS

This application makes reference to and claims the priority benefit of the following U.S. Provisional Patent Application No. 62/580,465 filed Nov. 2, 2017. The entire disclosure and contents of the foregoing Provisional application is hereby incorporated by reference.

FIELD OF THE INVENTION

The invention relates to methods for quantitative detection of DNA sequences, their incorporation in DNA libraries, and uses thereof

BACKGROUND

For decades, researchers have used Southern and Northern blotting to detect DNA and RNA sequences, respectively, in samples. These and other tools for analysis have developed over time to offer faster, easier, and more reliable approaches. Next Generation Sequencing (NGS), also known as Massive Parallel Sequencing (MPS), has recently emerged as a powerful tool for analysis of nucleic acids.

Splinted ligation technology is introduced in 2003 as a protocol for direct labeling and subsequent quantitative detection of small RNA sequences (see Moore M. J. and Query C. C., "Joining of RNAs by Splinted Ligation," *Methods Enzymol* 2000, 317:2003). In splinted ligation, two or more RNA fragments are joined using bridging splint DNA templates, thus creating complexes nicked at the ligation substrate site. Despite the absence of an amplification step, the protocol yields results at least fifty times more sensitive than those from Northern blots, making RNA detection from extremely small samples now possible.

Sequence tagging technology is predominantly used for RNA analysis. However, it has been modified for use with DNA (see Gansauge M. T. and Meyer M., *Nature Protocols* 8, 737-748 (2013) and Gansauge et al. "Single-Stranded DNA Library Preparation from Highly Degraded DNA Ssing T4 DNA Ligase," *Nucleic Acids Res* 2017). But despite these advances in sequence tagging technology, there remains a need in the art for protocols which offer sensitive and straightforward methods for preparing DNA libraries.

SUMMARY

According to a first broad aspect of the present invention, there is provided a method comprising the following steps: (a) treating a nucleic acid with bisulfite to convert non-methylated cytosines in the nucleic acid into uracils while leaving methylated cytosines unchanged to form a treated nucleic acid strand that is part of two joined nucleic acid strands; (b) ligating a first adapter to a 3' end of the treated nucleic acid strand to thereby form a once adapter ligated nucleic acid strand, the first adapter having a first protruding random sequence that is at least 3 bases long and that acts as a splint for the two joined nucleic acid strands; (c) ligating a second adapter to a 5' end of the once adapter ligated nucleic acid strand to thereby form a twice ligated nucleic acid strand, the second adapter having a second protruding random sequence that is at least 3 bases long and that acts as a splint for the two joined nucleic acid strands; and (d) performing polymerase chain reaction (PCR) amplification on the twice ligated nucleic acid strand to thereby generate copies of the twice ligated nucleic acid strand.

BRIEF DESCRIPTION OF THE DRAWINGS

The invention will be described in conjunction with the accompanying drawings, in which:

FIG. 8 is a table showing sequence metrics for whole genome bisulfite libraries;

FIG. 9 is a table showing read coverage and correlation of methylation between SPLAT and high coverage reference data;

FIG. 11 is a table showing correlation of DNA methylation levels of CpG sites with binned coverage in SPLAT with the high coverage reference libraries;

FIG. 14 is a table showing performance metrics for various WGBS library preparation methods, including a WGBS library preparation method according to one embodiment of the present invention;

FIG. 16 are graphs of: read coverage and methylation levels across a 3.5 Mb region of chromosome 12, a zoom-in view of a CpG poor 7.3 kb intergenic region on chromosome 12 and zoom-in view of a 6.4 kb region containing a methylated CpG island on chromosome 19 for various sequencing library preparation methods, including a method according to one embodiment of the present invention;

FIG. 18 is a table showing global methylation levels in the CHG and CHH (where H represents either A, T or C but not G) sequence context are low (0.3-1%), indicating that the bisulphite conversion rates are >99% in all libraries;

FIG. 19 is a table showing average methylation across mitochondrial CpG sites;

FIG. 20 is a table showing a summary of within read methylation for an analysis of individual reads with two or more CpG sites;

FIG. 22 is a table showing correlation coefficients for comparison between technical replicates for various WGBS method;

FIG. 23 is a table showing reduced-representation-bisulphite-sequencing (RRBS) and SureSelect MethylSeq libraries;

FIG. 27 is a table which shows numbers of low- and un-methylated regions as identified by MethylSeekR;

FIG. 28 is a table showing the read coverage of CpG sites in different WGBS libraries;

FIG. 29 is a table showing the annotation of low coverage CpGs (covered by two or fewer reads) to genomic features in NEBNextUltra libraries (216-219 M read pairs analyzed);

FIG. 31 is a table showing a comparison of the characteristics of different WGBS library preparation technologies.

DETAILED DESCRIPTION

Figure 1:
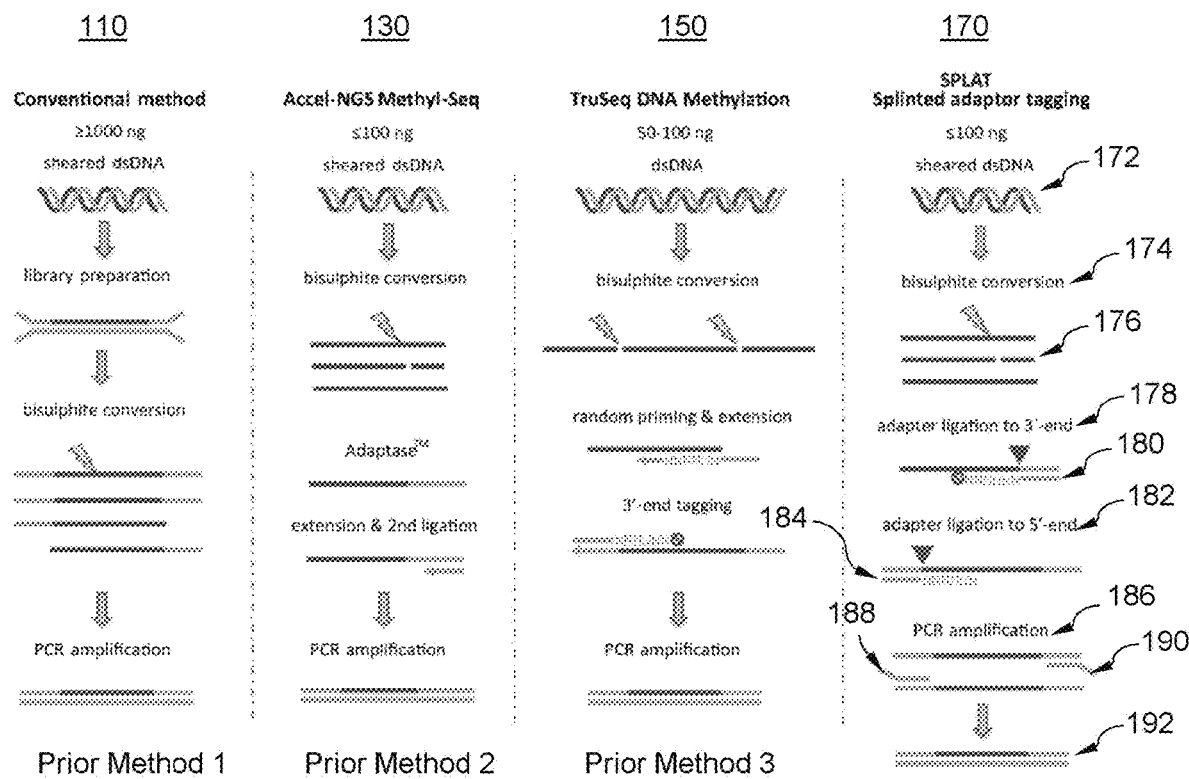
FIG. 1 is a diagram showing three prior library preparation methods (Prior Methods 1 through 3) for whole genome bisulphite sequencing, as well as a method for library preparation according to one embodiment of the present invention.

It is advantageous to define several terms before describing the invention. It should be appreciated that the following definitions are used throughout this application.

Definitions

Where the definition of terms departs from the commonly used meaning of the term, applicant intends to utilize the definitions provided below, unless specifically indicated.

For the purposes of the present invention, directional terms such as "top," "bottom," "side," "front," "frontal," "forward," "rear," "rearward," "back," "trailing," "above", "below", "left", "right", "horizontal", "vertical", "upward", "downward", etc. are merely used for convenience in describing the various embodiments of the present invention.

For purposes of the present invention, the term "adapter" refers to a short single stranded or double stranded oligonucleotide of at least 3 bases, for example, 3 to 70 bases, such as 13 to 25 bases, that can be ligated to the ends of other DNA or RNA molecules.

For purposes of the present invention, the term "adapter tagging" refers to the ligation of adapters to nucleic acids with the aim to produce nucleic acids with 3' and 5'tags containing known sequences, in turn enabling detection or further analysis by next generation sequencing or by other nucleic acid detection technologies.

For purposes of the present invention, the term "bisulphite" (interchangeable with the term "bisulfite") refers to the conventional meaning of the term "bisulphite", i.e., any salt including the ion $HSO_3^-$ ion. An example of a bisulphite salt is sodium bisulphite.

For purposes of the present invention, the term "bisulphite-converted DNA" refers to DNA which has been treated with a bisulphite to convert a DNA's non-methylated cytosines into uracils, leaving methylated cytosines unchanged.

For purposes of the present invention, the term "DNA" refers to double-stranded (ds) and single-stranded (ss) DNA, unless specified otherwise and may refer to an entire DNA molecule or strand of DNA or a segment of a DNA molecule or strand of DNA, unless specified otherwise.

For purposes of the present invention, the term "nucleic acid" refers to any molecule that comprises nucleotides linked in a chain. Examples of nucleic acids are DNA and RNA.

For purposes of the present invention, the term "oligonucleotide" refers to the conventional meaning of the term "oligonucleotide", i.e., a short chain nucleic acid polymer of at least 3, for example from 3 to 70, such as from 13 to 25, nucleic acids in length.

For purposes of the present invention, the term "polymerase chain reaction (PCR) amplification" refers to the conventional meaning to the term PCR amplification, i.e., a technique used in molecular biology to amplify a single copy or a few copies of a segment of DNA across several orders of magnitude, generating thousands to millions of copies of a particular DNA sequence.

For purposes of the present invention, the term "protruding random sequence" refers to a portion of an adapter that is a random sequence of bases and that extends beyond one of a pair of joined nucleic acid strands for which the adapter acts as a splint. In one embodiment of the present invention, the protruding random sequence of an adapter being at least 3 bases long, such as from 3 to 20 bases long.

For purposes of the present invention, the term "shearing" refers to forming a fragment of a nucleic acid from a nucleic acid or a fragment of a nucleic acid that is smaller than the original nucleic acid or fragment of a nucleic acid that is sheared. Shearing techniques that may be used in the various embodiments of the method of the present invention include: acoustic shearing, sonication, hydrodynamic shearing, enzymatic shearing, chemical shearing, heat induced shearing, etc.

For purposes of the present invention, the term "ligation" refers to the conventional meaning of this term as the covalent linking of two ends of DNA or RNA molecules, most commonly done using DNA ligase, RNA ligase (ATP) or other enzymes.

For purposes of the present invention, the term "splinted ligation" refers to the conventional meaning of this term as the joining of two or more RNA (or DNA) fragments by including bridging splint DNA templates to create RNA:RNA/DNA (or DNA:DNA/DNA) complexes which are nicked specifically at the desired site of the ligation substrate.

For purposes of the present invention, the term "bridging splint DNA templates" refers to nucleic acids used for bringing two nucleic acids together by use of a splinted bridging sequence.

For purposes of the present invention, the term "DNA library" refers to the conventional meaning of this term as a collection of DNA fragments that may be sequenced on a next generation sequencer. The fragments that may be sequenced on a next generation sequencer may also be stored and propagated in a population of microorganisms through the process of molecular cloning.

For purposes of the present invention, the term "non-methylated cytosine" refers to cytosine which are converted to uracil through a process of deamination (i.e., the removal of an amino group).

For purposes of the present invention, the term "methylated cytosine" refers to cytosine which has been methylated (e.g., 5-methylcytosine) and which therefore cannot be converted to uracil through a process of deamination.

For purposes of the present invention, the terms "bisulphite sequencing" or "bisulfite sequencing" refer to the use of bisulphite/bisulfite treatment of DNA or RNA to determine its pattern of methylation.

For purposes of the present invention, the term "whole genome bisulphite sequencing" (hereafter referred to interchangeably as "WGBS") refers to sequencing of bisulfite converted DNA with next generation sequencing (NGS) to determine patterns of DNA methylation in the genome.

For purposes of the present invention, the term "SPlinted Ligation Adapter Tagging" (hereafter referred to interchangeably as "SPLAT") refers to the process of creating sequencing libraries from single-stranded nucleic acids by use of splinted ligation.

For purposes of the present invention, the term "oligo annealing" refers to the coming together of a short sequence of complementary nucleic acids to a nucleic acid template.

For purposes of the present invention, the term "next generation sequencing" (hereafter referred to interchangeably as "NGS," and also known as interchangeably as Massive Parallel Sequencing (MPS)) nominally refers to non-Sanger-based high-throughput DNA sequencing technologies where millions or even billions of DNA molecules may be sequenced in parallel, yielding substantially more throughput and minimizing the need for the fragment-cloning methods that are often used in Sanger-based sequencing of genomes.

For purposes of the present invention, the term "TruSeq DNA Methylation" refers to a commercially available WGBS library preparation protocol from Illumina, Inc.

For purposes of the present invention, the term "Accel-NGS Methyl-Seq" refers to a commercially available WGBS library preparation protocol from Swift Biosciences.

For purposes of the present invention, the term "RRBS" refers to reduced representation bisulfite/bisulphite sequencing.

For purposes of the present invention, the term "SureSelect Methyl-Seq" refers to commercially available targeted bisulfate/bisulphite sequencing protocol from Agilent Technologies.

For purposes of the present invention, the term "CpG" refers to a region of DNA where a cytosine nucleotide is adjacent to a guanine nucleotide in the 5'->3' direction. Accordingly, the term "CpG sites" refers to multiple CpGs, while the term "CpG islands" refers to regions of the genome where there is an overrepresentation of CpGs, typically the region is >200 bp long with >50% cytosine and guanine nucleotides.

For purposes of the present invention, the term "targeted capture methods" refers to methods where specific regions of the genome are enriched in a sequencing library.

For purposes of the present invention, the term "solution hybridization protocols" refers to targeted capture methods that are performed in solution.

For purposes of the present invention, the term "tagmentation-based whole genome bisulphite sequencing" (hereafter interchangeably referred to as "T-WGBS") refers to a WGBS library preparation method where adapters are ligated to double stranded DNA with the help of the Tn5 enzyme.

For the purposes of the present invention, the term "liquid" refers to a non-gaseous fluid composition, compound, material, etc., which may be readily flowable at the temperature of use (e.g., room temperature) with little or no tendency to disperse and with a relatively high compressibility.

For the purposes of the present invention, the term "room temperature" refers to the commonly accepted meaning of room temperature, i.e., an ambient temperature of 20° to 25° C.

For the purposes of the present invention, the term "comprising" means various compositions, compounds, components, elements, steps, etc., may be conjointly employed in embodiments of the present invention. Accordingly, the term "comprising" encompasses the more restrictive terms "consisting essentially of" and "consisting of."

For the purposes of the present invention, the terms "a" and "an" and similar phrases are to be interpreted as "at least one" and "one or more." References to "an" embodiment in this disclosure are not necessarily to the same embodiment.

For the purposes of the present invention, the term "and/or" means that one or more of the various compositions, compounds, components, elements, steps, etc., may be employed in embodiments of the present invention.

Unless otherwise specified, all percentages given herein are by weight.

Description

Sodium bisulphite treatment converts DNA's non-methylated cytosines into uracils, leaving methylated cytosines unchanged. Hence, methylation status at individual CpG sites can be read out by next generation sequencing. However, the strand-breaking side effect of sodium bisulfite treatment makes traditional methods of library preparation inefficient. Moreover, after bisulfite treatment the DNA is single stranded (ssDNA). High DNA input amounts are required to produce bisulfite sequencing libraries according to standard protocols, which may be prohibitive, e.g., methylation analysis using clinical samples.

The initial bisulphite treatment of the DNA, followed by adapter tagging of single stranded DNA (ss DNA) fragments, enables whole genome bisulphite sequencing (WGBS) using low quantities of input DNA.

It has surprisingly been found that a library preparation method according to one embodiment of the present invention can be based on the use of adapters with degenerate splints for ligation to single-stranded bisulfite-converted DNA. After oligo annealing, short stretches of dsDNA are produced and the ssDNA molecule is efficiently ligated to the sequencing adapter using standard T4 DNA ligase. This enables library preparation even with small amounts of DNA. Although in the described embodiment of the present invention, the protocol has been optimized for bisulfite converted DNA, in theory any single stranded DNA (ssDNA) may captured in to a sequencing library with this method. (The various processes and procedures that may be used in embodiments of the method of the present invention are also described and shown in Raine et al., "SPlinted Ligation Adapter Tagging (SPLAT), a Novel Library Preparation Method for Whole Genome Bisulphite Sequencing," *Nucleic Acids Research*, 2017, Vol. 45, No. 6, e36, the entire contents and disclosure of which is incorporated herein by reference.) While embodiments of the method of the present invention are applicable to all manner of ssDNA analysis, described in detail herein is a method according to one embodiment of the present invention of particular utility for analysis of bisulphite-converted DNA.)

Additionally, sodium bisulphite treatment of DNA combined with next generation sequencing (NGS) is a powerful combination for the interrogation of genome-wide DNA methylation profiles. Library preparation for WGBS is challenging due to side effects of the bisulphite treatment, which may lead to extensive DNA damage in the form of strand breakage. Recently, a new generation of methods for bisulphite sequencing library preparation have been devised. These methods for bisulphite sequencing library preparation are based on initial bisulphite treatment of the DNA, followed by adapter tagging of single stranded DNA (ssDNA) fragments, and enable WGBS using low quantities of input DNA. In one embodiment, the present invention presents a novel approach for quick and cost-effective WGBS library preparation that is based on splinted adapter tagging (SPLAT) of bisulphite-converted single-stranded DNA. In the examples described below, embodiments of the method of the present invention are compared against three commercially available WGBS library preparation techniques, two of which are based on bisulphite treatment prior to adapter tagging and one of which is a conventional WGBS method. Indeed, as further evidence of the unique and non-obvious nature of some embodiments of the method the present invention, an example is described below which provides a validation of an embodiment of the method of the present invention against three commercially-available WGBS library preparation techniques, two of which rely on bisulphite treatment (TruSeq DNA Methylation, Accel-NGS Methyl-Seq, and RRBS, target capture by SureSelect Methyl-Seq, and 450 k BeadArrays).

Also, methylation of cytosine (5-mC) residues in CpG dinucleotides is an epigenetic modification that plays a pivotal role in the establishment of cellular identity by influencing gene expression. In somatic mammalian cells, the majority of CpG sites are methylated. However, CpG sites located in regions of increased CG density, known as CpG islands, generally have low levels of CpG methylation (1). On the molecular level, it is well known that CpG methylation leads to X-chromosome inactivation, genomic imprinting, regulation of gene expression and suppression of transposable elements. Disruption of DNA methylation patterns is associated with disease, and particularly with cancer (2). These findings have spurred the development of technologies for genome wide DNA methylation profiling. The HumanMethylation450 BeadChip assay (450 k Bead Arrays, Illumina) has so far been the most frequently used platform for human studies. However, with the advent of high throughput sequencing techniques there has been a rapid development of methods that interrogate a larger proportion of the CpG sites in any genome, which can interrogate from a few million CpG sites up to the whole methylome, which in humans consists of 28 million CpG sites. Sodium bisulphite treatment of DNA converts non-methylated cytosines into uracils, whilst methylated cytosines remain unchanged (3). Hence, methylation status at individual CpG sites can be read out by sequencing or genotyping (4-6). Methods for genome-wide DNA methylation analysis that rely on bisulphite conversion of DNA include BeadArrays (7, 8) reduced-representation-bisulphite-sequencing (RRBS) (9-12), targeted capture methods (13-16), and WGBS. The 450 k and 850 k (EPIC) BeadArrays interrogate 2-4% of human CpG sites that are preselected based on various annotated features such as genes, promoters, CpG islands and regulatory elements such as enhancers. Targeted capture methods may be designed to interrogate any region of the genome using, e.g., bisulphite padlock probes (13, 14) or in solution hybridization protocols (15-17). The latter is implemented in several commercial kits, such as SureSelect Methyl-Seq (Agilent Technologies) and SeqCap Epi systems (Roche NimbleGen). RRBS uses restriction enzyme digestion to enrich for regions of high CpG content, such as CpG islands and promoters in any genome (9-12).

WGBS is the ideal choice for many DNA methylation studies since it allows for unbiased genome-wide profiling at single-base resolution. However, a drawback of WGBS is that it is still costly to perform on large sample sets. Moreover, conventional sample preparation methods for WGBS typically require microgram amounts of DNA, which may be prohibitive for many human disease applications and sample types, for example, rare cell types or small tissue biopsies where obtaining microgram amounts of DNA is not feasible. The strand breaking side effect of sodium bisulphite treatment renders the majority of sequencing library constructs unamplifiable during PCR and sequencing cluster generation. Using low amounts of input DNA is feasible, albeit at the expense of low complexity of the sequencing libraries and high redundancy of the obtained sequence reads caused by the large number of amplification cycles required. Tagmentation-based whole genome bisulphite sequencing (T-WGBS) (18) is developed for low DNA quantity library construction, but a major drawback to this approach is that the tagmentation is performed prior to bisulphite conversion and thus extensive amplification may still be required.

In order to circumvent the damage of library constructs, methods have been designed in which sequencing adapters are incorporated after bisulphite treatment (hereafter referred to as 'post bisulphite' methods) (19, 20). Various examples of such methods as well as an embodiment of the method according to the present invention are shown in FIG. 1. A conventional method is shown in column 110. AccelNGS Methyl-Seq protocol (Swift Biosciences) is shown in column 130, Illumina's TruSeq DNA Methylation kit's method is shown in column 150. The splinted adapter tagging (SPLAT) of bisulphite-converted single-stranded DNA method according to one embodiment of the present invention is shown in column 170. In the pioneering post bisulphite method PBAT (post bisulphite adapter tagging) which is not shown in FIG. 1 but similar in concept to the method shown in column 150, sequencing adapters are attached by two rounds of random primer extension using the bisulphite converted ssDNA as the initial template. PBAT enabled PCR-free WGBS libraries to be constructed from DNA quantities in the nanogram range (19) and has paved the way for further developments, such as Illumina's TruSeq DNA Methylation kit shown in column 130. Notably, a modified version of the PBAT protocol is recently used for single cell methylation profiling (21). An alternative approach for post bisulphite library preparation is implemented in the AccelNGS Methyl-Seq protocol (Swift Biosciences), shown in column 130, whereby a low complexity sequence tag is added to the 3' end of the ssDNA in order to serve as a scaffold for the attachment of sequencing adapters.

Principles of Library Preparation Methods for Whole Genome Bisulphite Sequencing:

According to the conventional method (see column 110 in FIG. 1) methylated adapters are ligated to double stranded sheared DNA fragments. The constructs are then bisulphite converted prior to amplification with a uracil reading PCR polymerase. The Accel-NGS Methyl-Seq method (see column 130 in FIG. 1) uses the proprietary Adaptase™ technology to attach a low complexity sequence tail to the 3'-termini of pre-sheared and bisulphite-converted DNA, and an adapter sequence. After an extension step a second adapter is ligated and the libraries are PCR amplified. The TruSeq DNA Methylation method (formerly EpiGnome) (see column 150 in FIG. 1) uses random hexamer tagged oligonucleotides to simultaneously copy the bisulphite-converted strand and add a 5'-terminal adapter sequence. In a subsequent step, a 3'-terminal adapter is tagged, also by using a random sequence oligonucleotide and the libraries are PCR amplified.

In the method according to one embodiment of the present invention (see column 170 in FIG. 1), sheared double stranded DNA 172 is subject to a bisulphite converson at step 174 which produce bisulphite converted single DNA strands 176. At step 178, adapters with a protruding random hexamer are annealed to the 3'-termini of single stranded DNA 176. The random hexamer acts as a 'splint', indicated by arrow 180 and the adapter sequence is ligated to the 3'-termini of single stranded DNA 176 using standard T4 DNA ligation. A modification of the last 3'-residue of the random hexamer is required to prevent self-ligation of the adapter. At step 182, adapters with a 5'-terminal random hexamer overhang is annealed to ligate the 5'-termini of single stranded DNA 176, also using T4 DNA ligase. Finally, at step 186, the libraries are PCR amplified using a uracil reading polymerase to produce DNA copies 192.

Having described the several embodiments of the present invention in detail, it will be apparent that modifications and variations are possible without departing from the scope of the invention defined in the appended claims. Furthermore, it should be appreciated that all examples in the present disclosure, while illustrating many embodiments of the invention, are provided as non-limiting examples and are, therefore, not to be taken as limiting the various aspects so illustrated.

EXAMPLES

Illustrative examples of embodiments of the present invention are described below:

Example 1

Sample Source

Human genomic DNA from a lymphoblastoid B-cell line (NA10860) are obtained from the Coriell Institute for Medical Research. Genomic DNA from the pre-B acute lymphoblastoid leukemia cell line REH (22) is isolated using the AllPrep Universal kit (Qiagen). DNA is quantified using the Qubit dsDNA BR Assay Kit (Thermo Fisher Scientific).

Protocol for Whole Genome Bisulphite Sequencing Library Preparation According to One Embodiment of the Present Invention Adapter Annealing Oligonucleotides are purchased from Integrated DNA Technologies. The 3'-adapter, ss1 (5'-GACGTGTGCTCTTCCGATCT-3' -amino-modifier (SEQ ID NO:1) (ss1-A) and 5'P-AGATCG-GAAGAGCACACGTC (SEQ ID NO:2) (ss1-B)) and 5'-adapter ss2 (5'-ACACGACGCTCTTCCGATCT (SEQ ID NO:3) (ss2-A) and 5'-AGATCGGAAGAGCGTCGTGT) (SEQ ID NO:4) (ss2-B)) are prepared by mixing the two oligonucleotides in the adapter pair to a final concentration of 100 μm in 50 μL of 100 mM NaCl, 10 mM Tris-HCl (pH 8.0), 0.5 mM EDTA. The oligonucleotides are annealed by heating the mixture to 95° C. and slowly decreasing the temperature to 10° C.

Library Construction

Genomic DNA is sheared to 300-400 bp (Covaris E220 System) and treated with sodium bisulphite (EZ DNA Methylation Gold, Zymo Research). The converted DNA is first treated with 5 units of polynucleotide kinase (Thermo Fisher Scientific), in T4 DNA ligase buffer (see buffer composition below) in a total volume 15 for 15 min at 37° C. The reaction mixture is heated to 95° C. for 3-5 min in a thermal cycler with a heated lid and then cooled on an ice/water bath. For the 3'-end ligation; adapter ss1 (final conc 10 μM), T4 DNA ligase buffer (40 mM Tris-HCl pH 7.8.10 mM MgCl$_2$, 10 mM DTT, 0.5 mM ATP), PEG4000 (5% w/v) and 30 units T4 DNA ligase (Thermo Fisher Scientific) and nuclease free water is added to the sample on ice, in a total volume of 30 μl. Ligation reaction mixtures are incubated at 20° C. for 1 h, and subsequently purified using AMPure XP (BeckmanCoulter) beads in a 2:1 bead to sample ratio and eluted with 10 µl nuclease free water. The eluted DNA is heated to 95° C. for 3-5 min in a thermal cycler with a heated lid and then cooled on an ice/water bath. For the 5'-end ligation; ss2 (final conc 10 µM), T4 DNA ligation buffer, PEG4000 (5%, w/v) and 30 units T4 DNA ligase (Thermo Fisher Scientific) and nuclease free $H_2O$ is added to the sample on ice, in a total volume of 20 µl. Ligation reaction mixtures are incubated at 20° C. for 1 h, purified using AMPureXP beads in a 2:1 bead to sample ratio and eluted in 10 µl nuclease free water. The libraries are amplified for 4 cycles using KAPA HiFi Uracil+ ReadyMix (KAPA Biosystems) and oligonucleotides:

(SEQ ID NO: 5)
5'-AATGATACGGCGACCACCGAGATCTACACTCTTTCCCTACACGACG
CTCTTCCGATCT-3' (PCR Universal primer), (SEQ ID NO:6)
5'-CAAGCAGAAGACGGCATACGAGATNNNNNNGTGACTGGAGTTCAGA
CGTGTGCTCTTCCGATCT-3' where NNNNNN denotes the Illumina index barcode sequence. The final libraries are purified twice with AMPure XP beads using a 1:1 bead to sample ratio.

Sequencing Libraries

The EZ DNA Methylation Gold kit is used for sodium bisulphite conversion of DNA according to the specifications specific for each library type as described below.

Conventional WGBS libraries are prepared using the NEBNextUltra kit. Briefly, 1 µg of gDNA is sheared to 300-400 bp (Covaris E220 system). End repair, A-tailing and ligation of methylated adapters is performed according to the manufacturer's protocol with the following minor modifications: ligated samples are cleaned using AMPure XP beads at a 2:1 bead to sample ratio prior to bisulphite conversion and PCR amplified for six cycles using the KAPA HiFi Uracil+ PCR polymerase.

The 'post-bisulphite' conversion WGBS libraries are prepared according to the Accel-NGS Methyl-Seq DNA library kit (Swift BioSciences) or the TruSeq DNA Methylation Kit (Illumina) according to the manufacturers' protocols. The Accel-NGS libraries are generated from 100 ng of sheared (350 bp, Covaris E220 System) gDNA that is subsequently bisulphite converted. Four cycles of PCR are used to amplify the Accel-NGS Methyl-Seq libraries. The TruSeq DNA Methylation libraries are generated from 100 ng of sodium bisulfite treated gDNA without pre-shearing. Nine cycles of PCR are used to amplify the TruSeq DNA Methylation libraries.

RRBS libraries are prepared by a single-tube workflow using NEBNextUltra reagents (NEBNextUltra EndRep/A-tailing module, Ligation module and Methylated Adapters, New England Biolabs). Briefly, 200 ng of gDNA in a total volume of 25 µl is digested for 16 h using 50 units of MspI in NEB2 buffer (New England Biolabs). After the incubation the reaction mixture is transferred to an end repair/A-tailing reaction mixture. End repair, A-tailing and ligation of methylated adapters are performed as recommended in the NEBNextUltra kit protocol. The adapter concentrations are reduced 10-fold in the ligation mixes (50 nM final concentration) compared to the manufacturer's instruction to avoid excessive formation of adapter dimers. After ligation the samples are purified with AMPure XP beads applying a 2:1 bead to sample ratio, prior to bisulphite treatment. Bisulphite-converted libraries are PCR amplified for eleven cycles using the Pfx Turbo Cx polymerase (Agilent Technologies). Two consecutive bead purifications with a 0.9:1 bead to sample ratio are performed to clear the PCR-amplified libraries from oligonucleotides and adapter dimers.

SureSelect Methyl-Seq (Agilent Technologies) libraries are prepared from 3 µg of gDNA following the manufacturer's protocol.

Sequencing and Data Analysis

Paired end sequencing (2×125 bp) is performed on a HiSeq2500 system using the TruSeq v4 chemistry (Illumina). The specific parameters for the programs used for mapping, quality assessment, and DNA methylation calling are provided in detail in FIG. 2.

Figure 2:
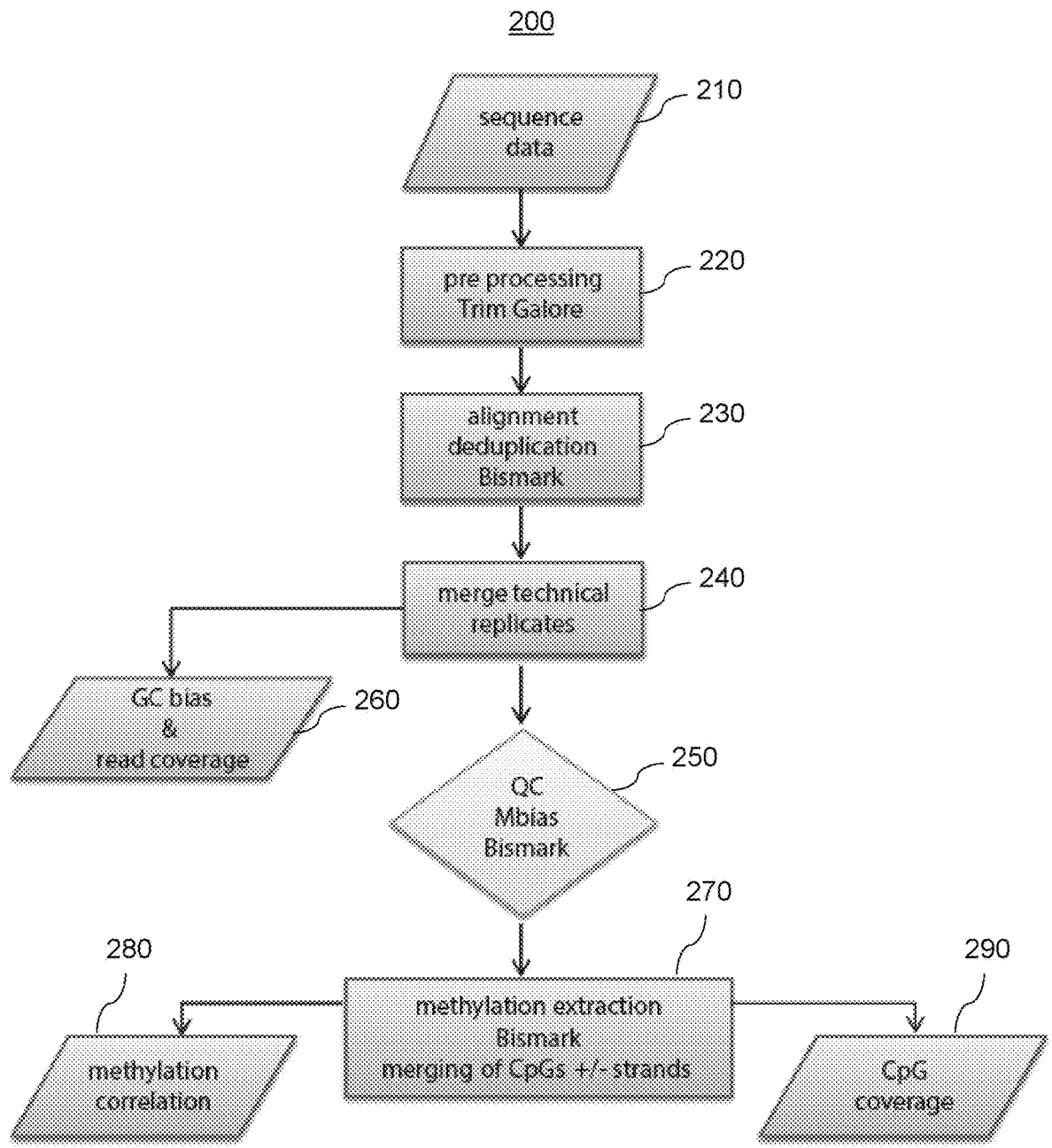
FIG. 2 is a flowchart showing whole genome bisulphite sequencing (WGBS) process according to one embodiment of the present invention.

As shown in WGBS process 200 of FIG. 2, sequence data is obtained at step 210. At step 220, adapter trimming and quality filtering of reads is performed with TrimGalore v0.37 (minimum adapter overlap of 1 bp and Q score cut off 20) specifying options; —paired, —trim1 AccelNGS Methyl-Seq reads are additionally trimmed 18 base pairs at the beginning of each read2 and at the end of each read1 by specifying options; —clip_R2 18 and —three_prime_clip_R1 18. At step 230, alignment to the reference genome is performed with Bismark v0.14 (bowtie2) using the default parameter settings. At steps 240 and 250, PCR duplicates are removed using the Bismark deduplication script and data from technical replicates is merged with Samtools. At step 260, GC bias and read coverage is analysed using Picard Tools, BEDTools v2.23.0 and Qualimap. At step 270, methylation calling is performed with Bismark specifying options; —no_overlap, —ignore and —ignore_r2. The decision if to exclude residues in the beginning or end of reads is based on the Mbias profile of each library (see FIG. 21). At step 270, methylation values on plus and minus strands ware combined using Bismarks coverage2cytosine option, specifying; —merge_CpG or alternatively by a custom R script. At steps 280 and 290, correlation of methylation and CpG site coverage is analysed from the Bismark output files using custom R scripts.

Briefly, quality control of sequencing data is performed with the FastQC tool. Sequence reads are quality filtered and adapters are trimmed using TrimGalore. Alignment to the human reference assembly GRCh37 and methylation calling is performed with the Bismark v 0.14 software (23) and the pipeline tool ClusterFlow v 0.4 http://www.clusterflow.io. GC bias metrics in sequencing data is analysed with Picard Tools (http://broadinstitute.github.io/picard/). Sequencing coverage across the whole genome and in genomic features is determined with Qualimap (24) and BEDTools (25). CpG site coverage and concordance of methylation calls is computed from the Bismark methylation extractor output files using custom R scripts. The cytosine methylation status is called per individual CpG sites as #C/(#C+#T) for CpG sites with at least 5× coverage. Thus methylation is detected if at least one methylated read is observed. CpG sites are annotated using BEDTools. Annotation files are downloaded from the UCSC Genome Browser or prepared from the GENCODE hg19 annotation by methods similar to those described in; https://www.gitbook.com/book/ycl6/methylation-sequencing-analysis. Hypomethylated regions are identified using MethylSeekR (26) and overlapping hypomethylated regions are determined using the 'findoverlaps' function in the R package GenomicRanges using default settings (27).

Example 2

Processing of Accel-NGS Methyl-Seq Reads

Figure 3:
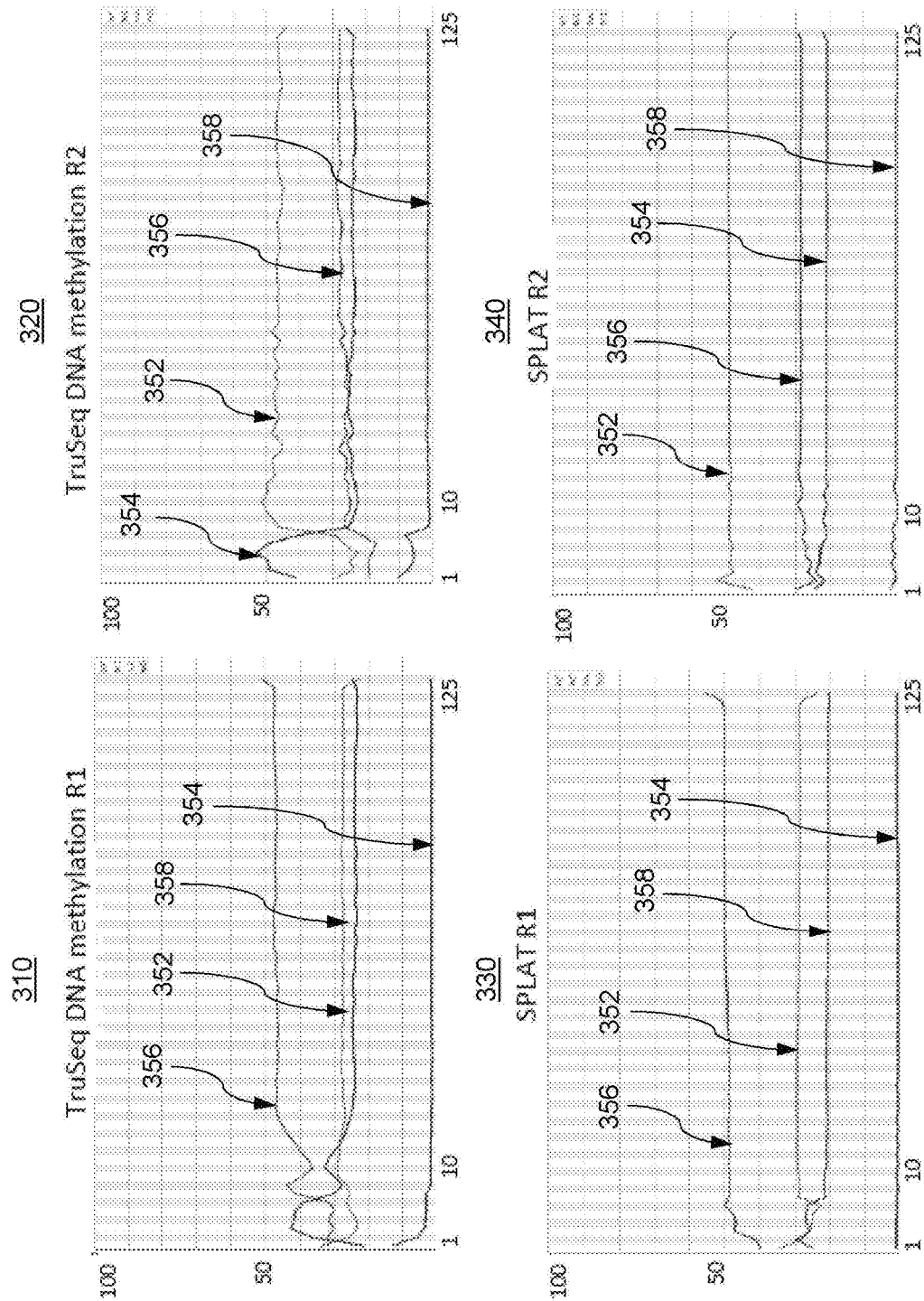
FIG. 3 are graphical base sequence content plots for a prior WGBS method, as well as for one embodiment of the method of the present invention generated by the FastQC program wherein the Y axis represents the % of all bases and the X axis represents the position in the read.
Figure 4:
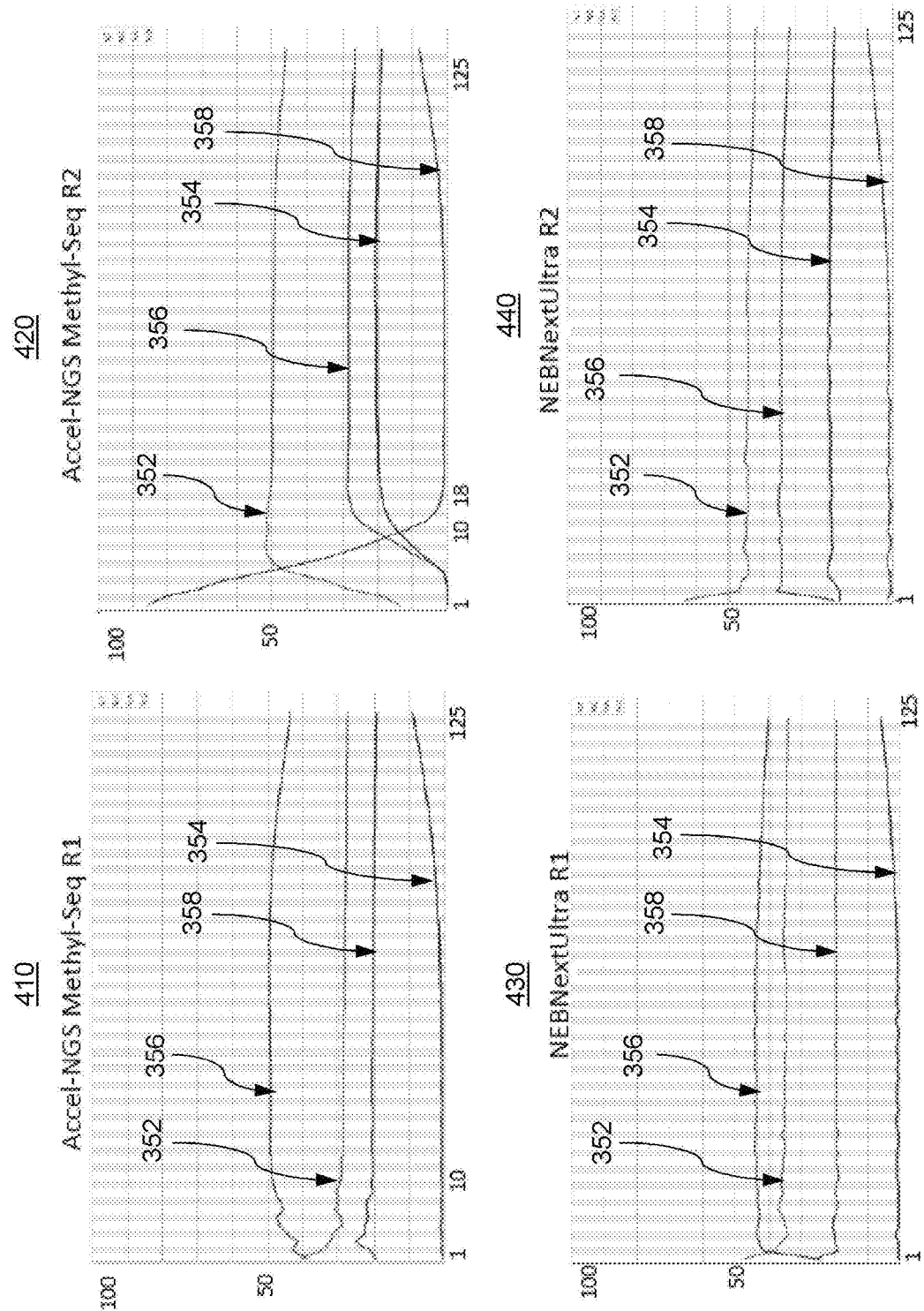
FIG. 4 are graphical base sequence content plots for two prior WGBS methods generated by the FastQC program.

A low complexity tag of varying length is added to the 3' termini of the ssDNA during the Accel-NGS Methyl-Seq library preparation (see FIGS. 1, 3 and 4), and these sequence tails are present at the beginning of all second read (R2) sequences. Since paired-end sequencing read lengths of 125 base pairs are close to the insert sizes of the libraries, the additional sequence tails in the Accel-NGS Methyl-Seq libraries are present at the end of many of sequences from the first read. The kit vendor suggests that trimming off 10 residues at the beginning of each R2 sequence and end of each R1 sequence for read lengths over 100 bp should be sufficient to remove most of the artificial sequence in the data. However, based on per base sequence content plots (see FIGS. 3 and 4 for per base sequence content plots for all WGBS methods) it is apparent that in this Accel-NGS Methyl-Seq data, the low complexity sequence tag may be up to 15-18 nucleotides in length. Thus trimming the first 18 residues of each R2 sequence and the end of each R1 sequence is performed to avoid methylation artefacts and improve alignment efficiency. FIGS. 3 and 4 show per base sequence content plots for the WGBS methods generated by the FastQC program. In FIG. 3, the X-aris shows the position in the read and the Y-axis shows the % of all bases. In FIGS. 3 and 4, green (indicated by arrow 352)=A, blue (indicated by arrow 354)=C, red (indicated by arrow 356)= T, black (indicated by arrow 358)=G. In plots 310 and 320 of FIG. 3, plots 330 and 340 of FIG. 3 and plots 430 and 440 of FIG. 4, are shown for adapter trimmed reads. In plots 410 and 420 of FIG. 4, is visualized that a low complexity sequence tag is added to the 3'end of single stranded bisulfite converted DNA during Accel-NGS Methyl-Seq library prep. Judged by the read 2 profile, a tail trimming of 15-18 residues is required to remove all artifacts from the library preparation.

DNA Methylation Analysis Using 450 k Bead Arrays

Genomic DNA (500 ng) is treated with sodium bisulphite (EZ DNA Methylation Gold) and the DNA methylation levels are measured using the Infinium HumanMethylation 450 k BeadChip Array (Illumina) according to the manufacturer's instructions. Raw beta-values are extracted from the arrays using the Genome Studio Methylation Module (Illumina) and methylation data from probes that hybridize to more than one genomic location and from probes with SNPs in the target regions of their 3'-ends are filtered out as previously described (28).

Figure 5:
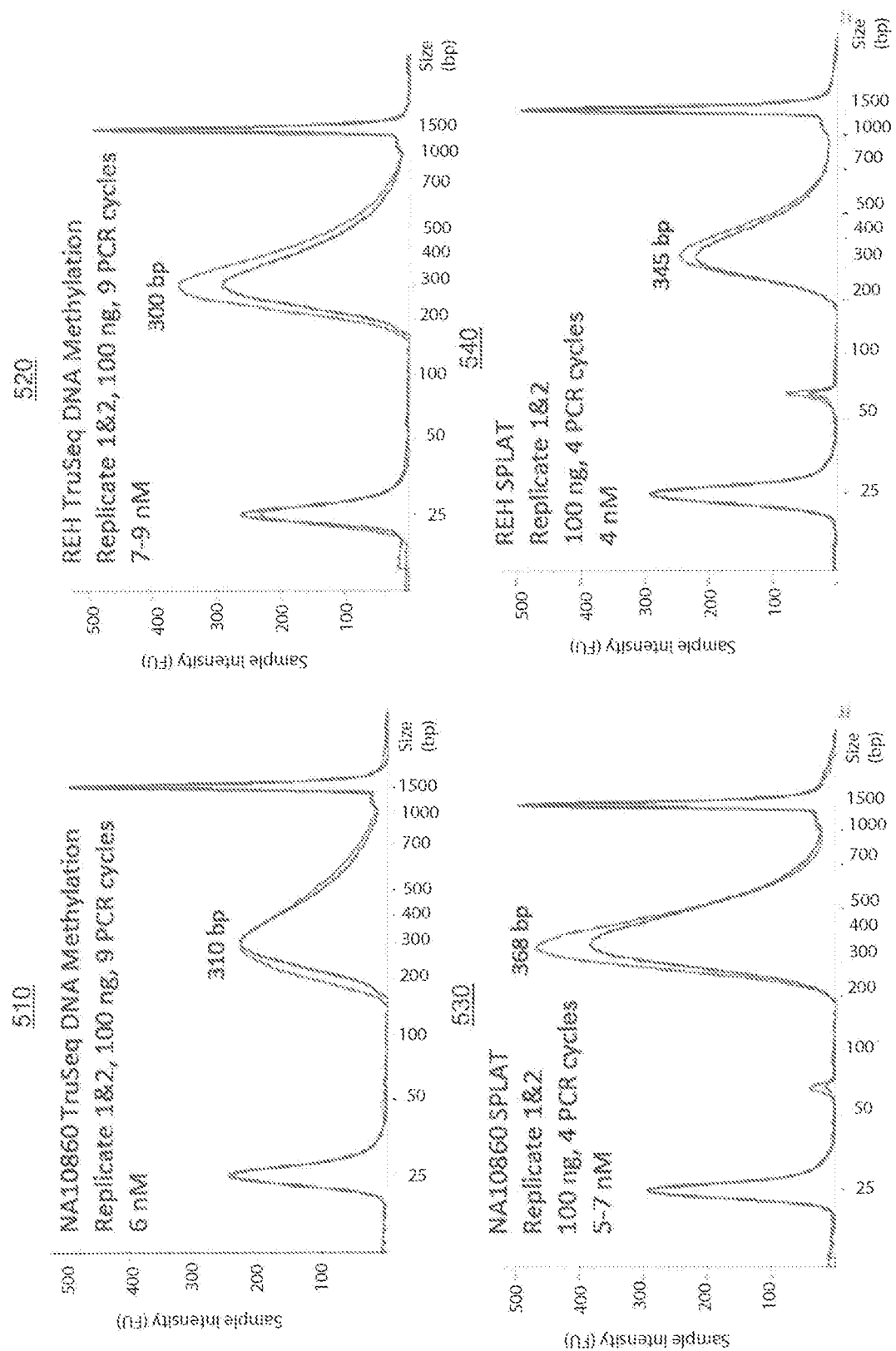
FIG. 5 are graphical size profile plots of WGBS libraries generated by one prior WGBS method, as well as by one embodiment of the method of the present invention, wherein the Y-axis represents sample intensity (in Fluorescence Units) and the X-axis represents the size (in terms of base pairs)
Figure 6:
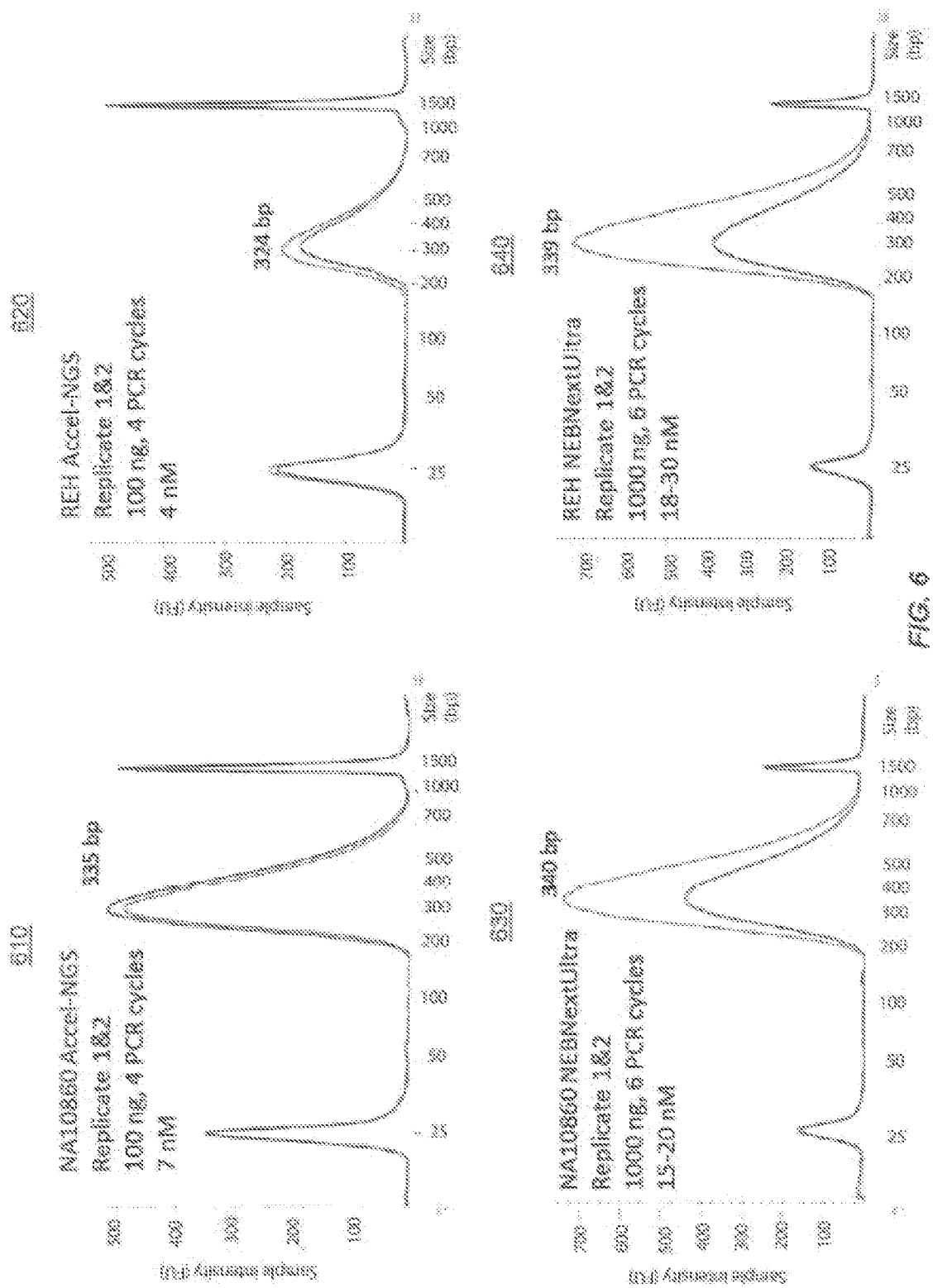
FIG. 6 are graphical size profile plots of WGBS libraries generated by two prior WGBS methods.
Figure 7:
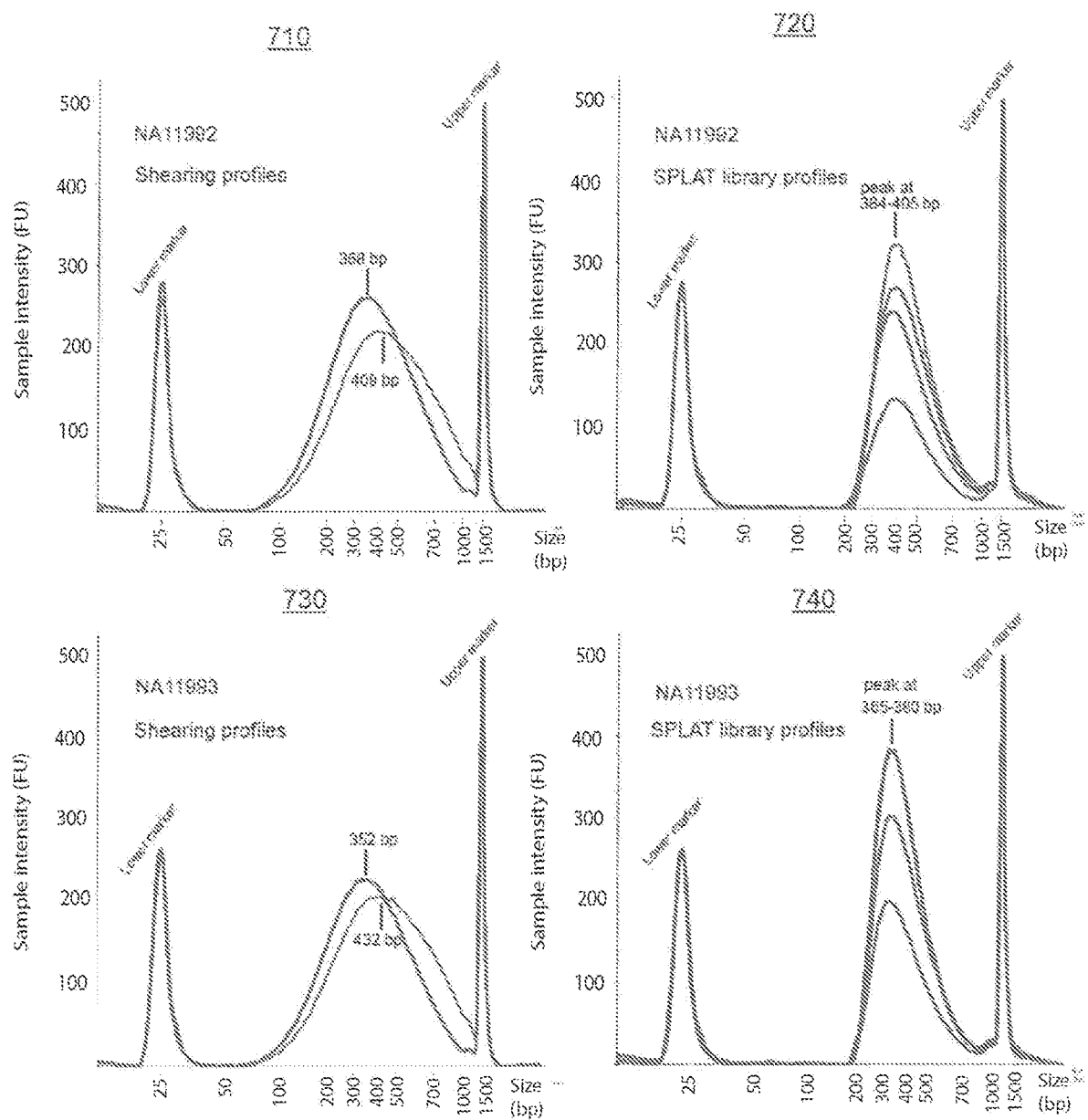
FIG. 7 are graphical size profile plots of eight SPLAT libraries generated from the lymphoblastoid cell lines NA11992 and NA11993.

Splinted Adapter Tagging (SPLAT) for Whole Genome Bisulphite Sequencing Library Preparation Embodiments of the present invention may also be used to provide SPLAT, which is an alternative method that introduces a new concept for efficient ligation of sequencing adapters to bisulphite converted single stranded DNA fragments. The SPLAT method takes advantage of splint oligonucleotides (29) to create short stretches of dsDNA fragments that allow subsequent ligation of sequencing adapters using standard dsDNA ligation with T4 DNA ligase, which is more efficient than ligation of ssDNA. SPLAT, which is outlined in FIG. 1 (together with the other library methods for WGBS) is a sensitive method, which uses affordable off-the-shelf enzymes. Using SPLAT with 100 ng of input DNA subjected to only four PCR amplification cycles (using KAPA HiFi Uracil+ polymerase) yields sufficient amounts of library for WGBS. Library size profiles and the results from library quantifications are shown in FIGS. 5, 6 and 7. The volume of the final libraries is 20 μl and the concentrations shown in the plots are determined using a Tape Station instrument. FIGS. 5 and 6 show size profile plots of WGBS libraries generated with four different methods: Size profile 510 of FIG. 5 is for the lymphoblastoid B-cell line NA10860 generated by TruSeq DNA Methylation. In FIG. 5, the X-axis shows the size in base pairs and the Y-axiss shows sample intensity in fluorescence units. Size profile plot 520 of FIG. 5 is for the B-cell leukemic cell line REH generated by TruSeq DNA Methylation. Size profile plot 530 of FIG. 5 is for the lymphoblastoid B-cell line NA10860 generated by a SPLAT method according to one embodiment of the present invention. Size profile plot 540 of FIG. 5 is for the B-cell leukemic cell line REH generated by a SPLAT method according to one embodiment of the present invention. Size profile plot 610 of FIG. 6 is for the lymphoblastoid B-cell line NA10860 generated by Accel-NGS. Size profile plot 620 of FIG. 6 is for the B-cell leukemic cell line REH generated by Accel-NGS. Size profile plot 630 of FIG. 6 is for the lymphoblastoid B-cell line NA10860 generated by NEBNextUltra. Size profile plot 640 of FIG. 6 is for the B-cell leukemic cell line REH generated by NEBNextUltra.

FIG. 7 shows size profile plots of eight SPLAT libraries generated from the lymphoblastoid cell lines NA11992 and NA11993. Profile plots 710 and 730 are for the gDNA (1000 ng) sheared to 300-400 bp using a Covaris E220 system (profile plots are shown prior to bisulfite conversion). Profile plots 720 and 740 are for the SPLAT library (color coded according to which sheared DNA they are derived from) using 100 ng of sheared and bisulfite converted gDNA. Libraries are PCR amplified for 4 cycles (KAPA HiFi Uracil+). The final volume of each library is 20 ul and the concentration (as measured by TapeStation) is 3-7 nM.

After bisulphite conversion, short double stranded adapters (20 nucleotides) comprising a random 3' overhang are annealed to the 3' ends of the ssDNA and ligated using T4 DNA ligase. Similarly in a second step, the 5' ends of the ssDNA are ligated using adapters comprising a random 5' overhang. To prevent self-ligation of adapters in the first ligation step, an amino modification (3' Amino Modifier, Integrated DNA Technologies) is added to the 3'-terminal nucleotide in the random hexamer oligo. In the second ligation step the oligo modification is not required. The libraries are subsequently amplified by PCR making use of the KAPA HiFi Uracil+ polymerase, which is capable of reading the uracil base and is compatible with oligos that contain Illumina flow cell binding and indexing sequences.

Figure 10:
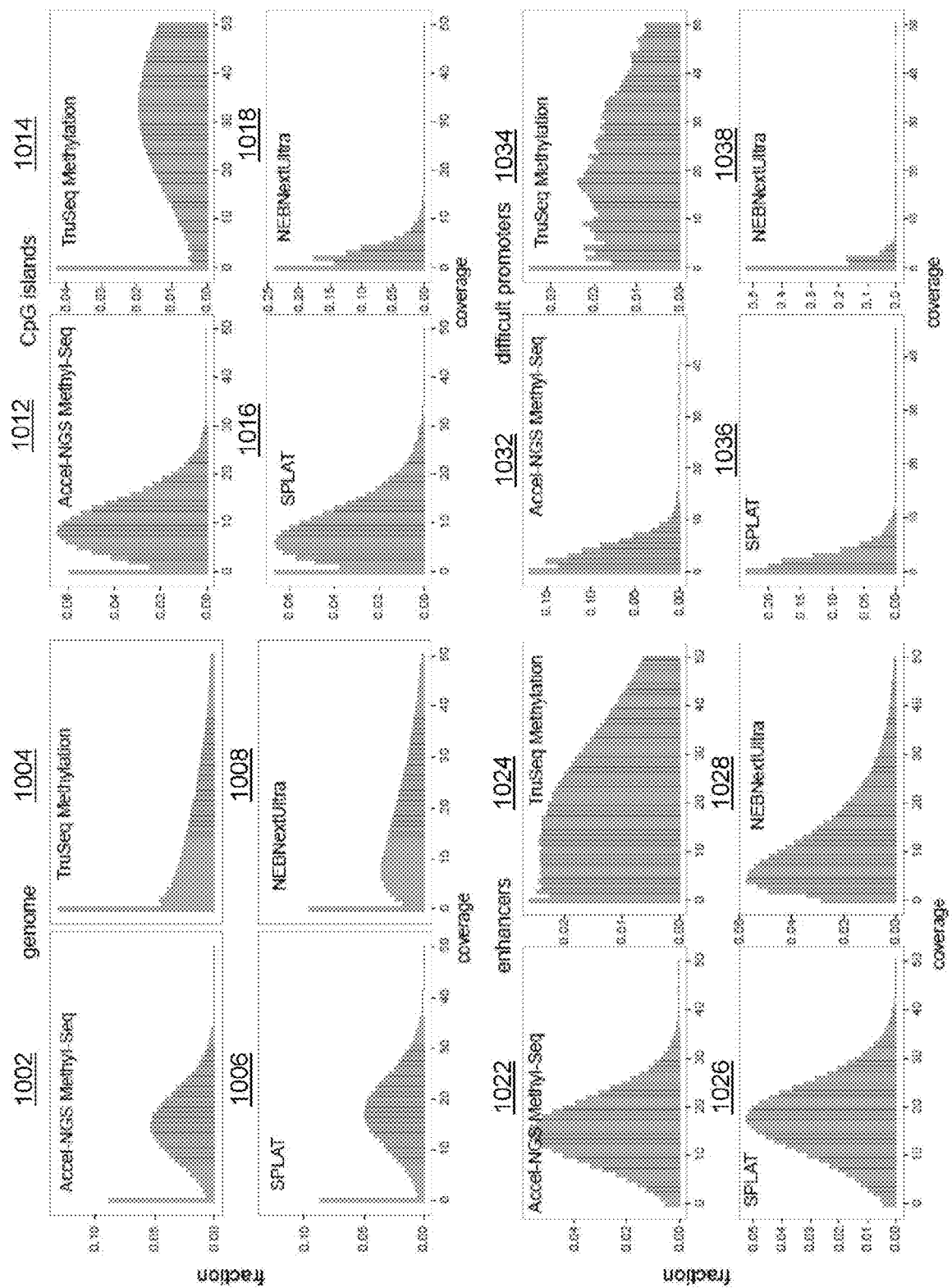
FIG. 10 are graphical plots of read coverage histograms for an NA10860 sample, wherein the Y-axis represents the fraction of the genome, and the X-axis represents coverage (i.e., read counts)

The SPLAT method according to one embodiment of the present invention is validated by performing WGBS of DNA from two different sources, namely the lymphoblastoid B-cell line NA10860 and the B-cell leukemic cell line REH (22). These two cell lines, an immortalized B-cell line and a cancer cell line are chosen to mirror samples with differing methylation profiles. Two SPLAT libraries are prepared from each cell line and each library is sequenced on one lane, PE125 base pairs using a HiSeq2500 machine (in total four SPLAT libraries). Data yields and mapping efficiencies are in the expected range for WGBS and the PCR duplication levels are very low (1-2%) in all four SPLAT libraries. Sequencing information, mapping efficiencies and PCR duplication levels are listed in Table 1 of FIG. 8. Data from the two technical replicates per cell type are merged prior to analysis and the final average read coverage is 16× and 22× in NA10860 and REH data, respectively. At CpG dinucleotide positions specifically, the average coverage is 13× and 17× in NA10860 and REH SPLAT data, respectively (Table 2 of FIG. 9). The SPLAT libraries from both cell types displayed uniform genome coverage, albeit coverage decreases in CpG islands and in very GC rich promoter regions (see FIG. 10). This is a commonly observed phenomenon in next generation sequencing (NGS) data and is thought to be a consequence of low PCR efficiency for GC-rich regions. In summary, WGBS libraries prepared with the SPLAT method display excellent global performance metrics such as data yield, mapping efficiency, PCR duplication rates and uniformity of coverage.

Validation of Methylation Calls in SPLAT Data Against High Coverage Reference Data Sets:

To obtain high coverage 'reference' methylation maps for both cell lines NA10860 and REH, WGBS data is merged from six sequencing libraries that are prepared using three different commercial kits (TruSeq DNA Methylation, Accel-NGS Methyl-Seq, NEBNextUltra). In this way two high coverage WGBS data sets are created with average read coverages of ~50× for use as reference data sets for the results from SPLAT (see Table 2 of FIG. 9). The concordance of methylation profiles between SPLAT and the reference data sets are investigated by comparing methylation levels computed across reads at individual CpG sites. To measure how the read coverage in SPLAT affects the accuracy of DNA methylation calls CpG sites are binned by coverage and measured the correlation with the methylation levels called in the high coverage reference data set for CpG sites with ≥20× coverage (see Table 3 of FIG. 11).

Figure 12:
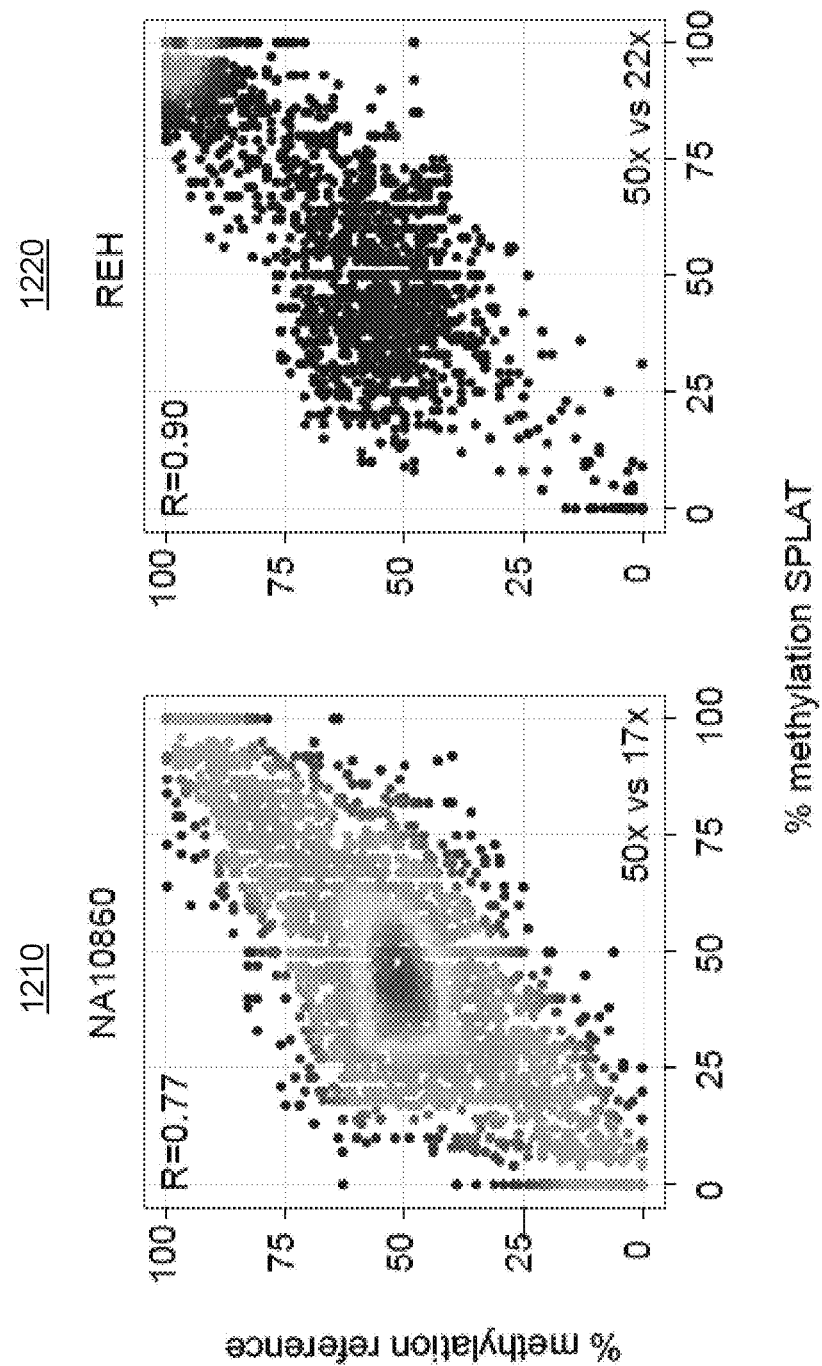
FIG. 12 are two graphical plots providing a comparison of methylation levels at individual CpG sites located throughout known imprinted regions in the high coverage reference data sets (y axis) and in SPLAT libraries (x-axis)
Figure 13:
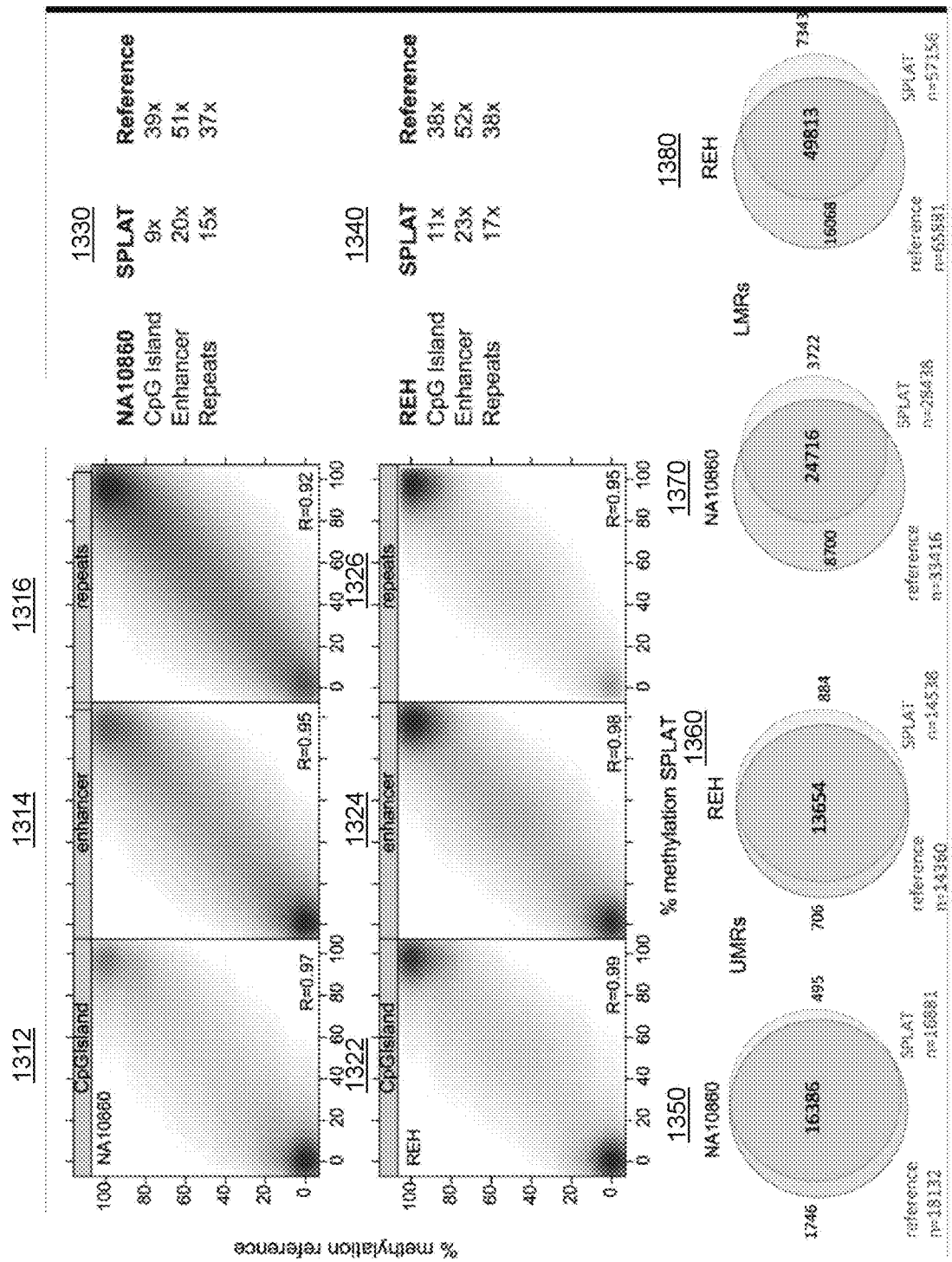
FIG. 13 are graphical plot comparisons of SPLAT with a high coverage reference dataset including: scatter plots showing a pairwise comparison of methylation levels at individual CpG sites in CpG islands, enhancers, and repetitive regions determined by SPLAT (x-axis) and the high-coverage reference WGBS data (y-axis) obtained by combining the data from TruSeq DNA Methylation, Accel-NGS and NEBNextUltra libraries with Pearson's correlation coefficients shown in the lower right corner of each scatter plot, two tables showing the mean read coverage of the CpG sites in CpG islands, enhancers and repeats for SPLAT and the high coverage reference data set, diagrams comparing the numbers and overlaps of un-methylated regions (UMRs) between SPLAT and high coverage reference WGBS data, and diagrams comparing the numbers and overlaps of lowly methylated regions (LMRs) in SPLAT and high coverage reference WGBS data, wherein in the Scatter plots (1312-1316), the darker areas represent where there are many CpG sites with similar or the same methylation values detected in the reference (Y axis) and SPLAT (X-axis), and which shows that there is a strong correlation, i.e., that SPLAT produces the same DNA methylation measurements as the reference dataset, and wherein in the Venn diagrams (1350-1380), each circle represents a number of a specific type or region found in the respective data sets, "LMRs" (or "UMRs") being colored by data set, wherein the part of the circles that overlap illustrates the degree of overlap between the two data sets, i.e., how many were found in both datasets, and wherein the non-overlapping portions of the circles represent the fraction of LMRs found only in the one data set.

As might be expected, the methylation calls are more accurate with increasing read-depth, however still at low coverage the correlation coefficient is >0.9. When comparing all CpG sites interrogated by five or more reads Pearson's R is 0.94 for NA10860 and 0.97 for REH. Pairwise comparisons are performed of methylation levels between SPLAT and the reference data sets from NA10860 and REH for CpGs located in CpG islands, putative enhancer regions and known repetitive elements (see plots 1312, 1314, 1316, 1322, 1324 and 1326 of FIG. 13). The mean read coverage of the CpG sites in these regions is shown in Tables 1330 and 1340 of FIG. 13. To investigate regions with intermediate methylation levels methylation levels are also compared at individual CpG sites located within 36 known imprinted regions where one of the alleles is expected to be fully methylated while the other is fully unmethylated (30). In the lymphoblastoid cell line (NA10860) a large fraction of the CpG sites located in the known imprinted regions displayed the expected methylation levels close to 50%. However, in the cancer cell line (REH) aberrant DNA methylation profiles that are indicative of loss of imprinting are observed (see FIG. 12). This is a common phenotype of cancer cells (31). FIG. 12 shows a comparison of methylation levels at individual CpG sites located throughout known imprinted regions in the high coverage reference data sets (y axis) and in SPLAT libraries (x-axis). FIG. 13 show a comparison of SPLAT with a high coverage reference dataset. Pairwise comparison of methylation levels at individual CpG sites in CpG islands, enhancers, and repetitive regions determined by SPLAT (x-axis) and the high-coverage reference WGBS data (y-axis) obtained by combining the data from TruSeq DNA Methylation, Accel-NGS and NEBNextUltra libraries. Pearson's correlation coefficients are shown in the lower right corner of each scatter plot are shown in plots 1312, 1314, 1316, 1322, 1324 and 1326 of FIG. 13. The mean read coverage of the CpG sites in CpG islands, enhancers and repeats for SPLAT and the high coverage reference data set are shown in Tables 1330 and 1340 of FIG. 13. Comparison of the numbers and overlaps of un-methylated regions (UMRs) between SPLAT and high coverage reference WGBS data are shown in diagrams 1350 and 1360 of FIG. 13. Comparison of the numbers and overlaps of lowly methylated regions (LMRs) in SPLAT and high coverage reference WGBS data are shown in diagrams 1370 and 1380 of FIG. 13.

Hypomethylated Regions in Whole Genome Bisulfite Sequencing Libraries Prepared with SPLAT:

An important aspect for determining the quality of a WGBS experiment is the ability for unbiased, genome-wide detection of regulatory regions. Therefore, as a second approach to validate the data from SPLAT, the MethylSeekR software is used for identification of regions belonging to one of two distinct classes: CpG-rich, completely unmethylated regions that correspond to proximal regulatory sites including promoters (UMRs) and CpG-poor, low-methylated regions that correspond to distal regulatory sites (LMRs) (26). The UMRs detected in the SPLAT libraries and the high coverage reference data set are highly overlapping (see diagrams 1350 and 1360 of FIG. 13). In total, 97% and 93% of the UMRs detected in NA10860 and REH cells, respectively, overlapped with the high coverage reference data set. Unlike UMRs, which contain regions with a high density of CpG sites that typically are completely unmethylated (mean methylation level 6.5%), LMRs are short regions with few CpG sites with more intermediate methylation levels (mean 18-22%) that are thought to be associated with TF binding. In total 74% and 76% of the LMRs identified overlapped between SPLAT and the high coverage reference data set in NA10860 and REH cells, respectively (see diagrams 1370 and 1380 of FIG. 13). As expected, more LMRs are detected in the high coverage data than in SPLAT. Notably however, the fractions of LMRs that are uniquely identified in either data set is higher than that observed for the UMRs. For instance, in NA10860 cells 3722 LMRs are unique to the SPLAT data and 8700 LMRs are unique to the high coverage reference data. Because the uncertainty in estimation of methylation levels is dependent on coverage, especially so in the regions that display intermediate methylation levels, the sequencing coverage at these regions is looked at specifically. The average coverage of the regions with overlapping LMRs is 13-17× in the SPLAT libraries and 36× in the high coverage reference datasets. Despite this, when looking at the regions specifically called in the high coverage data set, but not in the SPLAT libraries these are covered at the same average sequence depth as the overlapping regions. When inspecting the non-overlapping regions in more detail it is found that the mean methylation levels are generally higher in the uniquely identified regions than in the overlapping LMRs (mean 18-22% methylation in overlapping LMRs and 26-29% methylation in unique LMRs). Thus methylation levels across unique LMRs deviated upwards towards software's upper limit cut-off for the defining a LMR (50% methylation), which may at least in part explain why these regions are called in one data set, but not in the other.

Comparison of SPLAT to commercial whole genome bisulphite sequencing methods. Next, the performance of SPLAT is assessed in individual comparisons with the three commercial methods for bisulphite sequencing library preparation. In two of the methods the DNA is bisulphite treated prior to adapter ligation using reagents from the TruSeq DNA Methylation (formerly EpiGnome) kit and the Accel-NGS Methyl-Seq kit, and a conventional method (NEBNextUltra), which is based on adapter ligation prior to bisulphite treatment (see FIG. 1). The TruSeq DNA Methylation protocol makes use of the PBAT concept with oligos with degenerate 3' ends for adapter tagging, whilst the strategy for adapter tagging in Accel NGS Methyl-Seq is based on Adaptase™ technology (see FIG. 1). The two types of 'post bisulphite' WGBS libraries are prepared using 100 ng of input DNA, whilst 1000 ng of input DNA is used for the conventional NEBNextUltra libraries.

Sequencing Metrics:

WGBS libraries are sequenced in one lane per technical replicate using a Hiseq2500 instrument and 125 bp paired-end reads with v4 sequencing chemistry. Sequence reads from all libraries are pre-processed prior to alignment using the same parameters, with the exception of the Accel-NGS Methyl-Seq data that required additional processing to remove the low complexity sequence tags that are introduced during library preparation. To avoid biases in the comparison, the same parameters are used for alignment of all libraries with the Bismark software (23). Mapping rates are between 70% and 83% for each of the WGBS methods, which is acceptable as the reduced complexity of the reads is expected to have a negative impact on the alignment efficiency (see Table 1 of FIG. 8). The highest mapping efficiency (83%) is achieved for the SPLAT and Accel-NGS Methyl-Seq libraries. The PCR duplication rate is low for SPLAT, Accel-NGS Methyl-Seq and NEBNextUltra (1-2% per lane), while TruSeq DNA Methylation libraries displayed higher PCR duplication rates (12-17% per lane) (see Table 1 of FIG. 8).

Data from two technical replicates are merged prior to downstream analysis. The amount of sequence data generated, the data yield after alignment and removal of PCR duplicates, the average coverage, and the mean library insert sizes in the WGBS methods are listed in Table 4 of FIG. 14 which shows performance metrics for WGBS library preparation methods.

WGBS libraries have relatively short insert sizes and consequently suffer from significant adapter contamination, particularly when read lengths are ≥100 bp. It is observed that the shortest mean insert sizes of ~160 base pairs in the TruSeq DNA Methylation libraries and mean insert sizes between 170 and 195 bp for the other protocols (Supplementary Table S2). Lower mapping efficiencies, high duplication rates, and short insert sizes are factors that all contribute to considerable loss of data in WGBS. The data yield relative to the amount of raw sequencing data generated is lowest for the TruSeq DNA Methylation libraries, where only 55-58% of data is retained after pre-processing, alignment and de-duplication. The Accel-NGS Methyl-seq and NEBNextUltra libraries retained 65-71% of data (mean 68%). The SPLAT method retains 65-76% of the data, which on average is the method that retains the most data after filtering (see Table 4 of FIG. 14). Therefore, the average genome coverage ranges from 14× to 22× in the WGBS data sets. Prior to performing subsequent analyses, each of the WGBS data sets is down-sampled to approximately the same number of read pairs (218-219 M for NA10860 libraries, 211-216 M for REH libraries) to enable cross-method comparisons with the same amount of starting data.

Read Coverage of WGBS Libraries:

Most currently used next generation sequencing library preparation methods result in an under-representation of GC-rich regions, which originates at least in part, from PCR amplification (32,33). In WGBS data, the GC bias tends to be even more pronounced than in standard sequencing libraries and thus important GC rich regions (CpG islands) that are targets of DNA methylation, e.g. in cancer can be significantly underrepresented. It is determined that the normalized read coverage in 100 bp windows of increasing GC content in the human reference genome, and found that the methods for sequencing library preparation generate distinct biased GC profiles (see plots 1510 and 1520 of FIG. 15). In the NEBNextUltra libraries, coverage is skewed towards AT rich regions, while GC rich regions are poorly covered. In contrast, in TruSeq DNA Methylation libraries coverage is skewed towards GC rich regions. Accel-NGS Methyl-Seq and SPLAT libraries had more uniform GC bias profiles, where regions with extreme base compositions, either AT or GC rich, are underrepresented.

Sequence Bias in Whole Genome Bisulphite Sequencing Libraries

Figure 15:
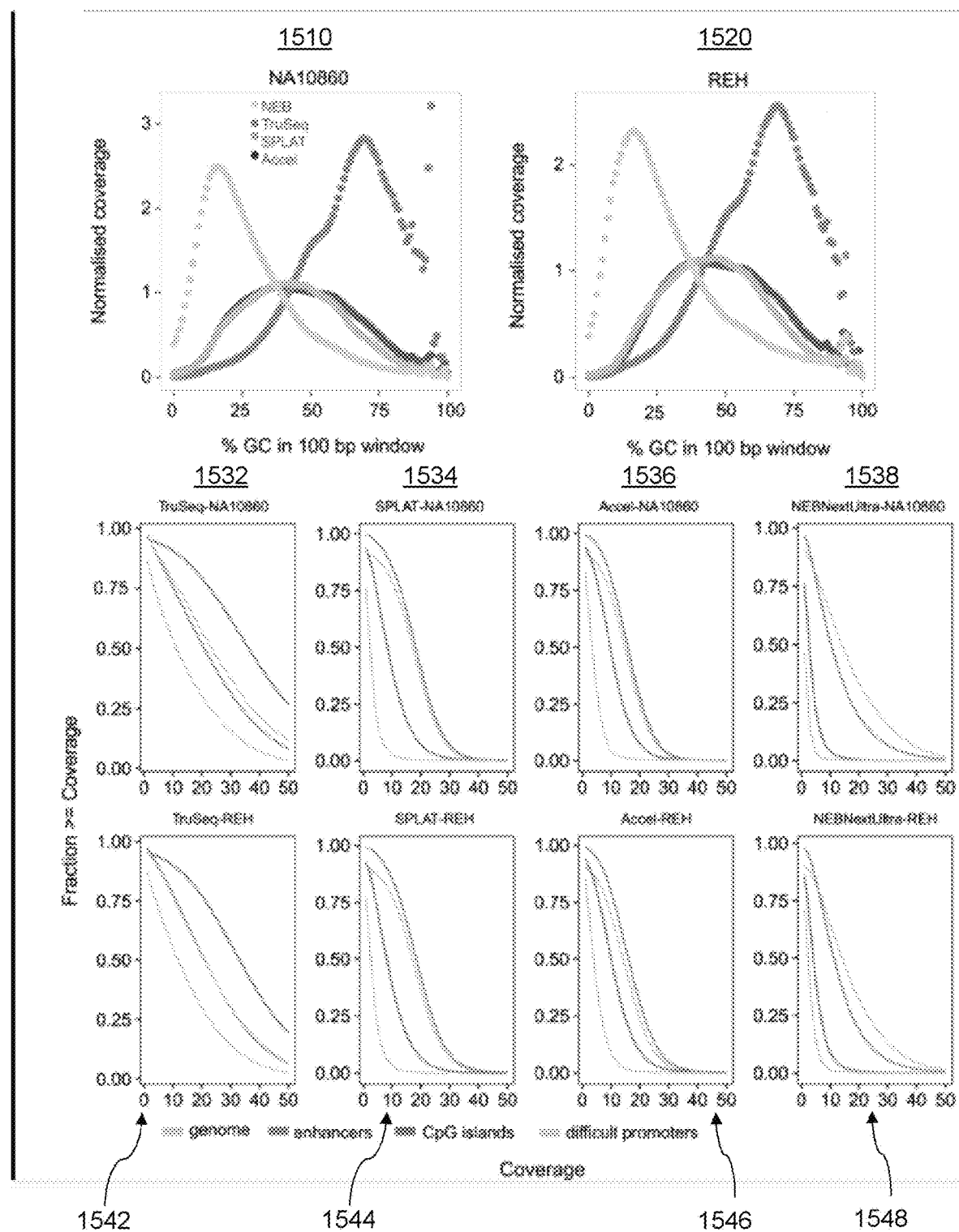
FIG. 15 are GC profile and coverage plots for various sequencing library preparation methods, including a method according to one embodiment of the present invention, wherein the Y-axis represents the fraction of the feature (i.e., features=genome, enhancers, CpG islands or difficult promoters, each represented by a differently colored line), and wherein the X-axis represents coverage (i.e., read count)

GC Bias Observed for the Different Methods:

The plots of FIG. 15 show the normalised coverage in 100 bp windows of increasing GC content in the human reference genome. NEBNextUltra libraries (see plots 1538 and 1548 of FIG. 15) have higher read coverages in AT rich regions, whilst the TruSeq DNA Methylation libraries (see plots 1532 and 1542 of FIG. 15) have increased read coverage of GC rich regions. The AccelNGS Methyl-Seq and SPLAT libraries (see, respectively, plots 1536 and 1546, and plots 1534 and 1544, of FIG. 15) display a lower GC bias, however regions with extreme GC content are not well represented.

Cumulative Coverage of Different Genomic Regions:

(Coverage plots in FIG. 15) for the whole genome are shown in green, CpG islands in purple, FANTOM5 enhancer regions in blue and a set of 1000 promoter regions that are difficult to sequence due to high GC content in grey.)

Next, the read coverage distribution generated by the WGBS library preparation methods between genomic regions is analyzed. Cumulative coverage plots for the whole genome, enhancer regions as defined by the FANTOM5 consortium (34), CpG islands and a set of 1000 promoters that have been characterized as 'difficult promoters', which have very high CG content and are notoriously difficult to sequence (35), are shown in plot 1520 of FIG. 15 for both cell types (see FIG. 10 for coverage histograms). Examples of genome browser views for the NA10860 cell type are shown in FIG. 16 to further illustrate coverage and methylation profiles. As is already inferred based on the GC bias profiles, the coverage of different genomic features varies in a characteristic manner between the WGBS methods. Out of the four methods, the Accel-NGS Methyl-Seq and SPLAT libraries displayed the most uniform coverage of the whole genome and of enhancer regions. However, for both these methods, the read coverage dropped in CpG islands and a substantial drop in coverage is observed in the 'difficult promoters'. The TruSeq DNA Methylation libraries displayed uneven overall coverage of the genome. However, GC-rich promoter regions and CpG islands generally displayed higher coverage than the genome on average and this is the only method that obtained adequate coverage of the 'difficult promoters'. The NEBNextUltra libraries on the other hand are characterized both by uneven whole genome coverage and a severe decrease in coverage in CpG islands and 'difficult promoters'. Importantly, the GC bias and coverage profiles are very reproducible between the two different cell types for each of the WGBS methods described here, which indicates these results are robust against any biological differences in total DNA methylation levels (see FIG. 15).

Genome Browser Views Displaying Coverage and Methylation Tracks for the Four Different WGBS Libraries Generated from the NA10860 Cell Type:

The blue tracks represent the read coverage, the red tracks represent the methylation levels across the regions and the green bars at the bottom of the panels represent CpG islands for genome browser view 1610 (read coverage and methylation levels across a 3.5 Mb region of chromosome), for genome browser view 1620 (zoom-in view of a CpG poor 7.3 kb intergenic region on chromosome 12; and for genome browser view 1630 (zoom-in view of a 6.4 kb region containing a methylated CpG island on chromosome 19.

Coverage Biases in Public WGBS Data Sets.

Figure 17:
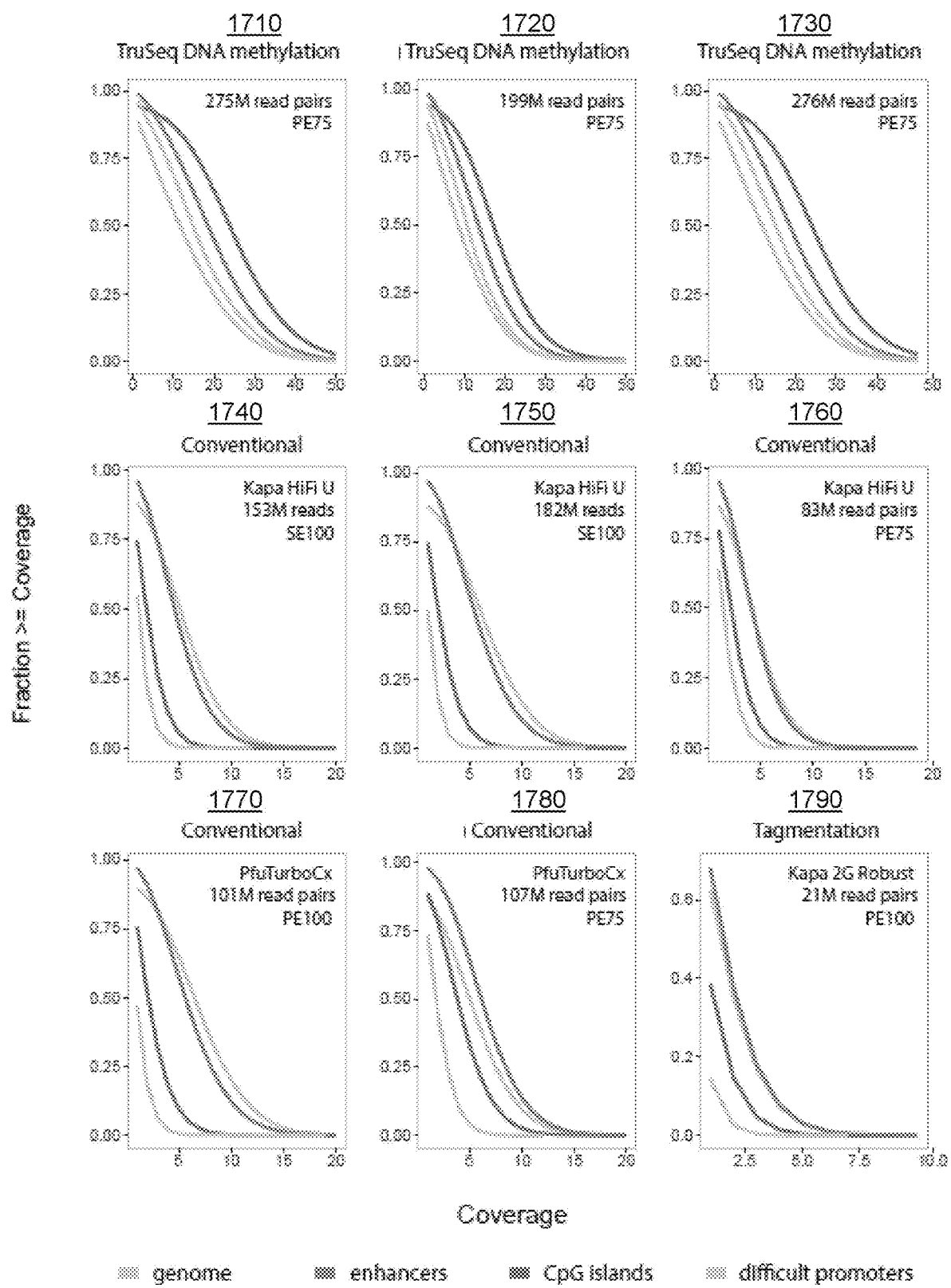
FIG. 17 are graphical coverage profile plots of public WGBS data sets downloaded from the short read archive (SRA), including TruSeq DNA Methylation libraries from lymphoblastoid cell line NA18507 (Accession #SRR1867799, SRR1867802, SRR1818296) and conventional WGBS libraries amplified with the KAPA HiFi Uracil polymerase, wherein the Y-axis represents the fraction of the feature (i.e., features=genome, enhancers, CpG islands or difficult promoters, each represented by a differently colored line), and wherein the X-axis represents coverage (i.e., read count)

It should be noted that the findings presented herein represent observations in the laboratory at a given point in time. To investigate if the observed biases in genomic and CpG site sequence coverage are reproducible between labs and not only characteristic to the sequencing library preparations, human WGBS data sets according to one embodiment of the present invention are downloaded from the NCBI Sequence Read Archive (SRA) from different library preparation protocols and analysed their coverage profiles. See FIG. 17, which shows coverage profiles profiles 1710, 1720 and 1730 of public WGBS data sets downloaded from the short read archive (SRA) for TruSeq DNA Methylation libraries from lymphoblastoid cell line NA18507 (profile 1710 for Accession #SRR1867799, profile 1720 for SRR1867802, and profile 1730 SRR1818296); coverage profiles 1740, 1750 and 1760 of Conventional WGBS libraries amplified with the KAPA HiFi Uracil polymerase for SRR1045663:Spleen (profile 1740), SRR1045744:Bladder (profile 1750), and SRR1536575:HCT116 colorectal cancer cell line (profile 1760); and coverage profiles 1770, and 1780 and 1790 of Conventional WGBS libraries amplified with the PfuTurbo Cx polymerase for SRR948844:B-lymphocytes (profile 1770), SRR096827: human stem cells 1 (profile 1780), and Tagmentation-WGBS library SRR447397: lymphoblastoid cell line GM20846 (profile 1790). (Coverage plots in FIG. 17 for the whole genome are shown in green, enhancer regions in blue, CpG islands in purple, and a set of 1000 promoter regions that are difficult to sequence due to high GC content in grey).

First, three TruSeq DNA Methylation libraries from the human lymphoblastoid cell line NA18507 obtained from the Blueprint consortium (GSE66285) are assessed in which it is observed the same trend towards increased coverage of CpG rich regions, including difficult promoters, as in our data. Second, five conventional human WGBS data sets originating from five various tissue types in which libraries are amplified using the two most commonly used uracil reading PCR polymerases (KAPA HiFi Uracil+ or PfuTurbo Cx) and one tagmentation-based WGBS data set (18,36-38) are evaluated. The coverage profiles from these libraries are very similar to those in libraries according to one embodiment of the present invention (see FIG. 15). As in SPLAT, Accel-NGS Methyl-Seq and NEBNextUltra libraries, a common feature is a decline in coverage over CpG rich regions and difficult promoters.

Determination of DNA Methylation Levels and Quality Control of Methylation Calls:

Global methylation levels in the CHG and CHH (where H represents either A, T or C but not G) sequence context are low (0.3-1%), indicating that the bisulphite conversion rates are >99% in all libraries (see Table 5 of FIG. 18, shows global cytosine methylation in CpG, CHH and CHG context).

An alternative method to assess bisulphite conversion rates is to determine the methylation levels in mitochondrial DNA, which is presumed to be unmethylated in human samples (39). It is found that the average methylation levels across mitochondrial CpG sites are very low in the SPLAT, Accel-NGS Methyl-Seq and NEBNextUltra libraries as expected. However, the average mitochondrial CpG methylation levels originating from TruSeq DNA Methylation libraries are consistently high (see Table 6 of FIG. 19, which shows average methylation across mitochondrial CpG sites).

The reason for this bias is unknown, but could be due to incomplete bisulphite conversion of the circular mitochondrial DNA. Furthermore, individual reads with two or more CpG sites are analyzed to determine the concordance of the methylation state of each cytosine position in a CpG context in each read (see Table 7 of FIG. 20 which shows a summary of each read methylation).

The proportion of reads with concordant methylation states is extremely similar between methods, however the proportion of reads available for such an analysis (containing ≥2 CpG sites) varied greatly between the methods, namely only 17-18% of the reads from NebNextUltra libraries, 22-26% of Accel-NGS and SPLAT libraries, and 35-36% of TruSeq DNA Methylation libraries. This result mirrors the coverage bias discussed above.

Figure 21:
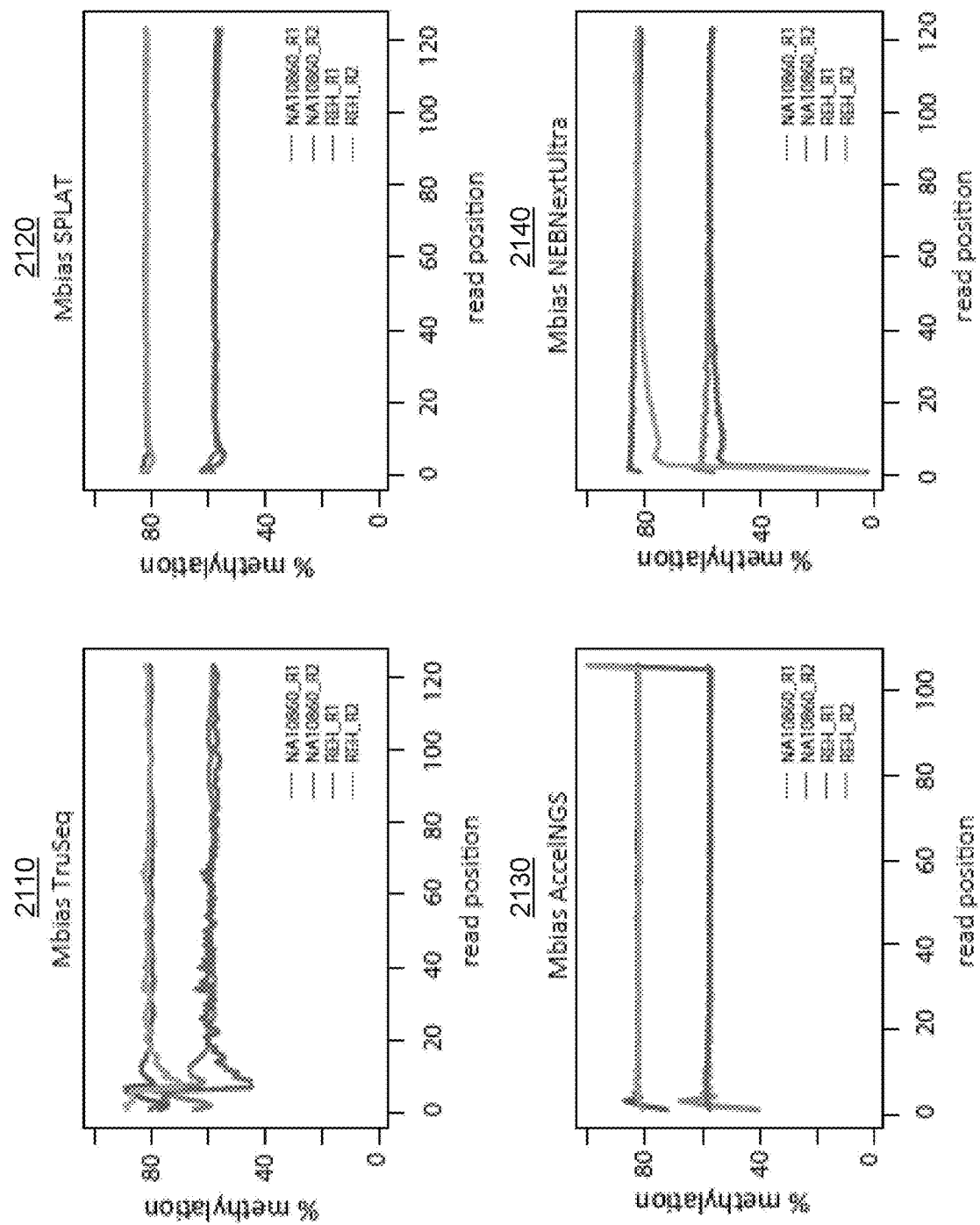
FIG. 21 are graphical plots showing Mbias profiles for visualization of methylation biases across NGS reads.

M-bias plots are frequently used for quality control of bisulphite sequencing data and are useful for detection of methylation biases at the ends of sequence reads (40). In an unbiased sequencing library the methylation levels should be independent of read position, and thus the mean methylation levels plotted against read position should form a horizontal line. Only the SPLAT libraries are unbiased in this parameter. FIG. 21 shows Mbias profiles. The decision whether to exclude bases in the beginning of reads from the methylation calling is based on Mbias profiles. Mean methylation is plotted against read position and nonbiased libraries should exhibit a horizontal line. In the TruSeq DNA Methylation libraries the first six residues of each read are excluded from the methylation calling. In NEBNextUltra libraries the first two residues of read2 are excluded. In Accel-NGS Methyl-Seq libraries the first 2 residues of read1 and the last residue of read2 are excluded (in addition to trimming the cytosine tails). In SPLAT libraries no residues are excluded from the methylation calling.

The M-bias profiles in the TruSeq DNA Methylation libraries fluctuate, particularly at the beginning of the reads. Thus to avoid biases in methylation levels in the TruSeq DNA methylation libraries the first six residues of each read from methylation calling are excluded. The NEBNextUltra libraries exhibits a sharp decrease in methylation levels at the beginning of the second read, which is characteristic for conventional library preparation protocols where end repair of sheared dsDNA fragments is performed with unmethylated cytosines. Thus, the first two bases of each read from methylation calling are excluded. The M-bias profiles for Accel-NGS Methyl-Seq libraries (after removing the sequence tails) also display a small dip in the beginning of the first read and a spike at the end of the second read and accordingly these three bases are excluded from the methylation calling.

Figure 25:
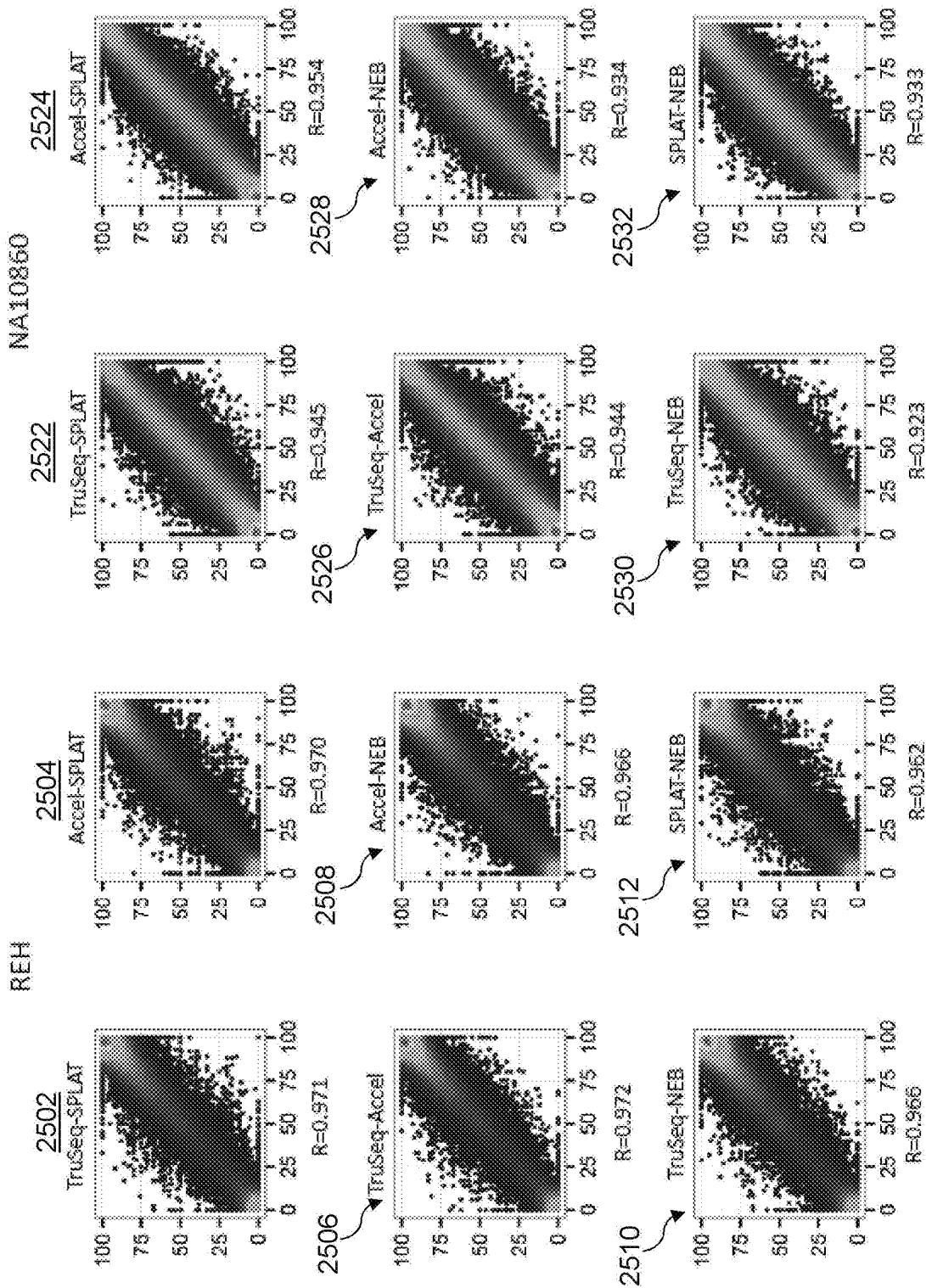
FIG. 25 is a set of graphical scatterplots showing average methylation in enhancer regions in scatterplots showing the correlation of average methylation in FANTOM5 enhancer regions, across WGBS library preparation methods, wherein the Y axis represents % methylation in the dataset and the X-axis represents % methylation in the dataset.

Concordance of Methylation Levels Across Methods:

Next pair-wise comparisons are performed of the methylation levels computed across reads at individual CpG sites between methods for both cell types (see Table 2610 of FIG. 25). First, the correlation between the methylation levels are obtained by the WGBS methods and those with 450 k Bead Arrays are measured. Using a minimum of 5-fold or higher coverage in the WGBS libraries, the concordance of methylation levels between 450 k Bead Arrays and all WGBS methods is excellent (Pearson's R=0.91-0.95 for NA10860 and 0.93-0.96 for REH). Concordance of the methylation levels across the four WGBS library preparation methods is also high (Pearson's R=0.88-0.91 for NA10860 and 0.90-0.95 for REH), with the exception of the methylation levels originating from NEBNextUltra libraries, which consistently displayed lower correlation coefficients in all pairwise comparisons. The correlation coefficients for comparison between technical replicates for each WGBS method are given in Table 8 of FIG. 22, which shows a correlation of methylation between technical replicates.

In the same pair-wise manner, there is also found a high degree of correlation between the methylation levels determined by WGBS, RRBS, and the SureSelect Methyl-Seq methods (Pearson's R=0.93-0.97 for NA10860 and 0.95-0.98 for REH) (see Table 9 of FIG. 23, which shows sequence metrics for RRBS and SureSelect MethylSeq libraries).

Figure 24:
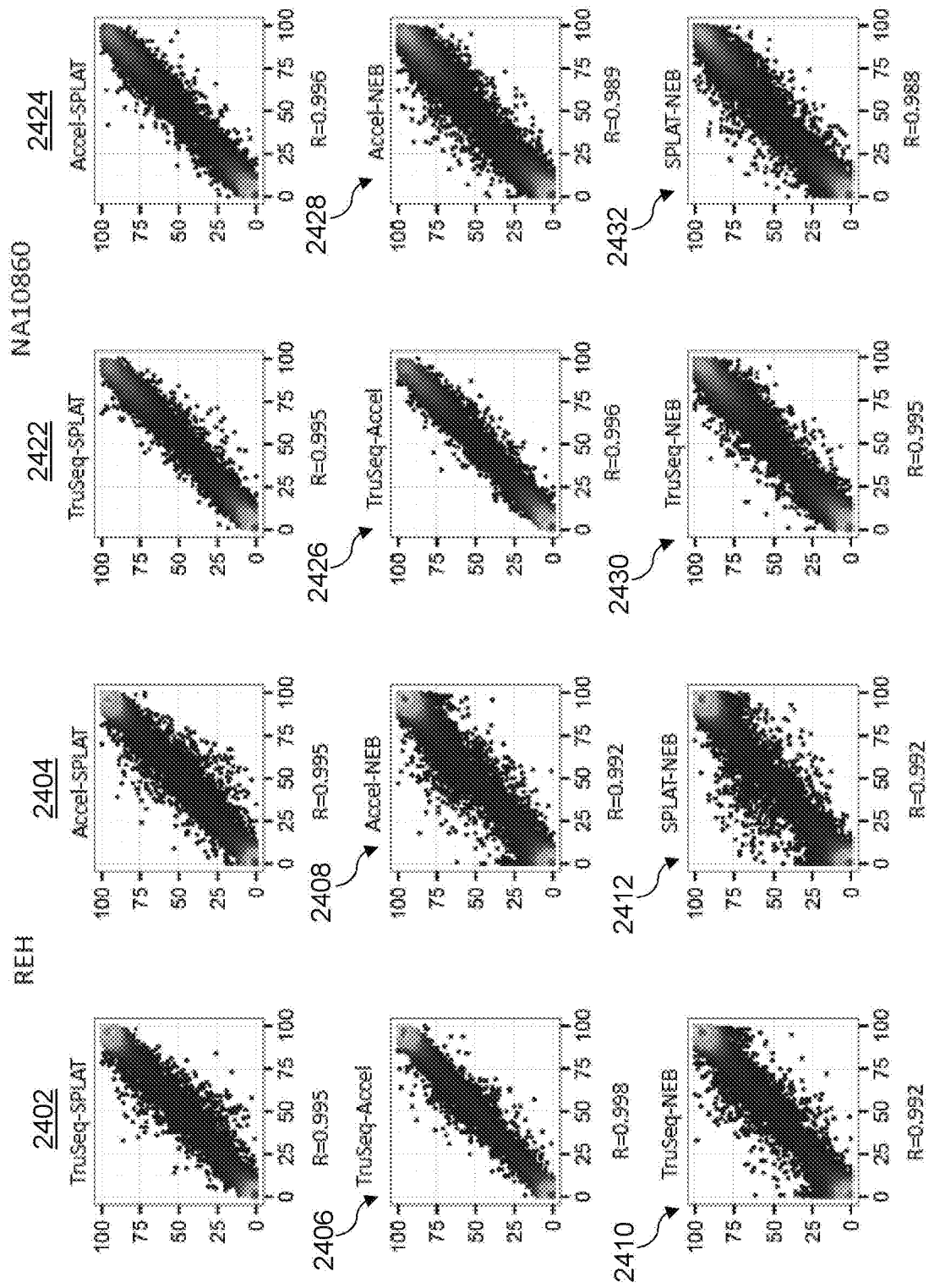
FIG. 24 is a set of graphical scatterplots showing the correlation of average methylation in CpG Islands, across WGBS library preparation methods.

Generally, the correlation coefficients are higher for pair-wise comparisons in the REH sample, presumably due to the fact that a larger proportion of the of the CpG sites in REH cells, compared to the normal B-cell line, are either completely methylated or unmethylated. Differences in methylation levels at individual CpG sites may be due to differences in read coverage at the particular site, and therefore the concordance of methylation levels across functionally different genomic regions was also assessed, which is less sensitive to variance in read coverage. The concordance between regional mean methylation levels across CpG islands and FANTOM5 enhancer regions is high between WGBS methods (Pearson's R=0.92-0.99), FIG. 24 shows average methylation in CpG islands in scatterplots showing the correlation of average methylation in CpG Islands, across WGBS library preparation methods. Regions with an average CpG site coverage below 4× are excluded from the comparison.

FIG. 25 shows average methylation in enhancer regions in scatterplots showing the correlation of average methylation in FANTOM5 enhancer regions, across WGBS library preparation methods. Regions with an average CpG site coverage below 4× are excluded from the comparison.

The mean methylation levels across CpG islands showed excellent correlations (>0.99) in all comparisons between the 'post bisulphite' WGBS methods. Similarly, for these methods the methylation level correlation is also high across enhancer regions (Pearson's R=0.94-0.97). Again, lower concordance is observed in the comparisons with NEBNextUltra libraries (for enhancer regions; Pearson's R=0.92-0.96 compared to 0.94-0.97 for comparisons solely between 'post bisulfite' methods).

Figure 26:
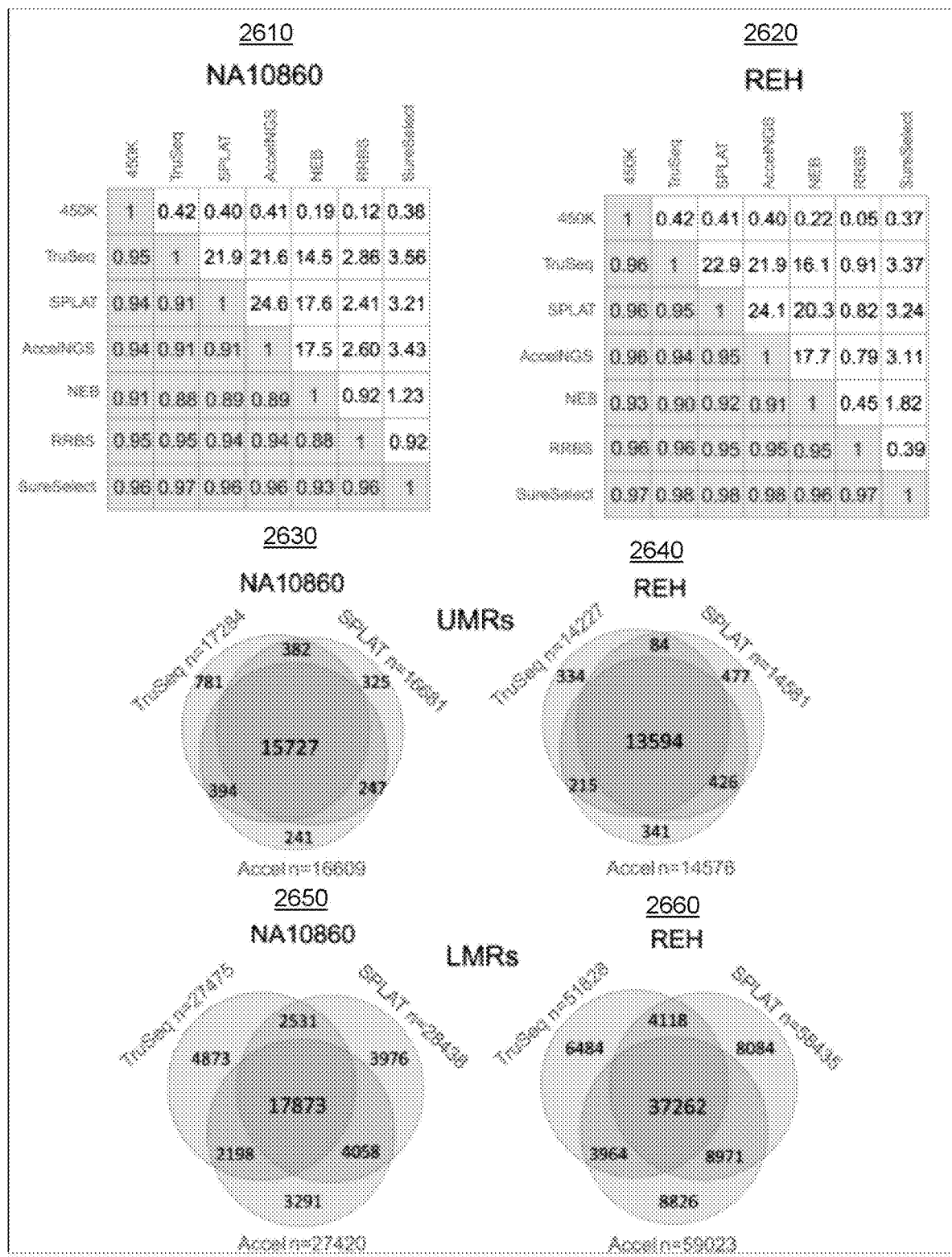
FIG. 26 are correlation matrixes showing pairwise comparison of methylation levels at individual CpG sites with, Pearson's correlation coefficients shown to the left of the diagonal, as well as Venn diagrams showing overlap of unmethylated and lowly methylated regions in three post bisulfite methods.

Concordance of Methylation Levels Across Methods:

Tables 2610 and 2612 of FIG. 26 shows pairwise comparison of methylation levels at individual CpG sites, Pearson's correlation coefficients are shown to the left of the diagonal. The numbers of CpG sites (in millions) included in each comparison are shown to the right of the diagonal. Venn diagrams 2630 and 2640 of FIG. 26 show the numbers and overlaps of un-methylated regions (UMRs) detected in the three 'post-bisulphite' library preparation methods. Venn diagrams 2650 and 2660 of FIG. 26 show the numbers and overlaps of low methylated regions (LMRs) detected in the three 'post-bisulphite' library preparation methods.

In summary, the 'post bisulphite' libraries yielded overall higher concordance in methylation calls both between the WGBS libraries and each of the other non-WGBS methods than the traditional WGBS method that is used herein.

Comparison of Hypomethylated Regions in WGBS Libraries.

Next LMRs and UMRs are analyzed in the different WGBS data sets. In line with the results described above, as many as 25% fewer UMRs and 50% fewer LMRs are detected in NEBNextUltra libraries compared to the other methods (see Table 10 of FIG. 27, which shows numbers of low- and un-methylated regions as identified by Methyl-SeekR).

Therefore the overlap of LMRs and UMRs are only assessed in the 'post bisulphite' WGBS libraries. Between 90% and 96% of the UMRs detected in any given library overlapped with those detected in all of the libraries (Venn diagrams 2630 and 2640), therefore each of the 'post bisulphite' methods are accurate in detecting UMRs (methylation level mean 6%, median 4%). Comparable numbers of LMRs are identified by all of the 'post bisulphite' methods (27 475-28 438 for NA10860 and 51 828-59 023 for REH, see Venn diagram 2660 of FIG. 26). Similar to what is described in the previous section when comparing SPLAT to the high coverage reference data, the degree of overlap is lower (63-72%) than observed for the UMRs. The greatest number of LMRs overlapped between the SPLAT and Accel-NGS methods, presumptively due to the more even genome-coverage achieved with these methods. However, when inspecting the non-overlapping regions in more detail, despite that the coverage is similar in the regions containing unique and overlapping LMRs (12-16×) across the WGBS methods, it is found that methylation levels of unique LMRs (mean methylation 26-29%) is on average 10% higher than in the overlapping LMRs (mean methylation 16-20%).

Genome-Wide CpG Site Coverage Across Methods:

For each sequencing-based method and cell type the total number of CpG sites that are covered by five reads or more are measured (see Table 11 of FIG. 28). The SPLAT and Accel-NGS Methyl-Seq data sets gave the best overall and most even coverage of the CpG sites in the human genome with 88-90% of the total CpG sites covered by at least five reads. The corresponding proportions are 82-83% for TruSeq DNA Methylation and 62-67% and NEBNextUltra. The results from the WGBS methods are also compared to RRBS and SureSelect Methyl-seq libraries where 8-10% and 14% of the total CpG sites are covered by at least five reads, respectively (see Table 11 of FIG. 28 and Table 9 of FIG. 23).

Figure 30:
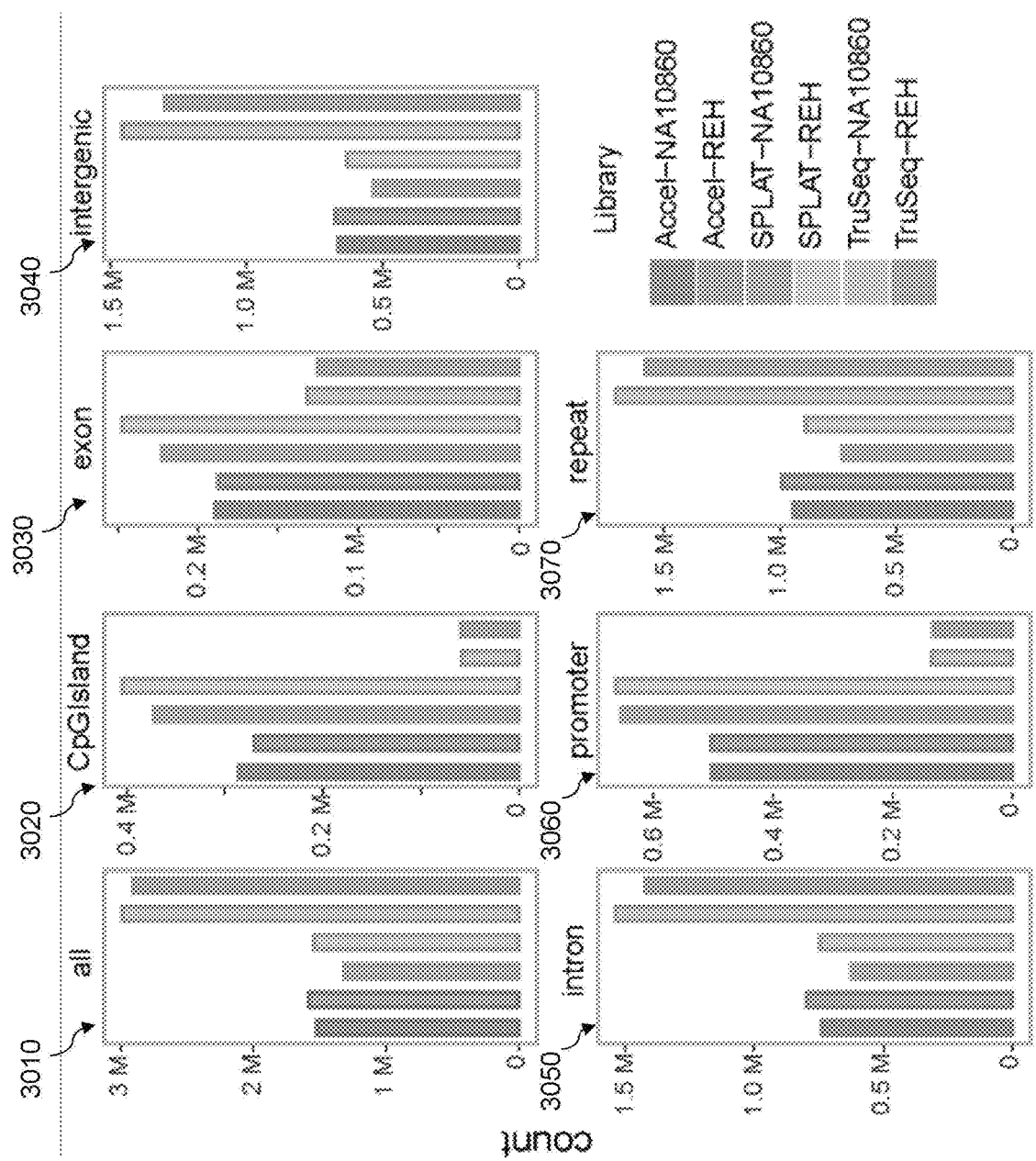
FIG. 30 are bar graphs showing a annotation of CpG sites with low coverage in the 'post bisulphite' WGBS methods.

Moreover, CpG sites are identified that are under-represented in each WGBS library by applying a coverage threshold of ≤2× and annotating the regions with poor coverage (see FIG. 30). Approximately 0.5 million CpG sites that are below this threshold are shared between all the 'post bisulphite' conversion libraries and are mainly annotated to intergenic regions, introns and repeats. Overall, the 3 M CpG sites with low coverage in TruSeq DNA Methylation libraries are over-represented in introns, intergenic regions and repetitive elements. The SPLAT and Accel-NGS Methyl-Seq libraries had 1.3-1.5 and 1.5-1.6 M low coverage CpGs, respectively. As expected, in these libraries there are more low coverage sites in CpG islands and promoter regions (TSS±200 bp) compared to TruSeq DNA Methylation libraries. The NEBNextUltra libraries had the largest number of low covered CpG sites (4.7-6.0M) and a large proportion of them are annotated to CpG islands and promoter regions, however many sites in intergenic regions and introns are also insufficiently covered (see Table 12 of FIG. 29 which shows the annotation of low coverage CpGs (covered by two or fewer reads) to genomic features in NEBNextUltra libraries (216-219 M read pairs analyzed)).

A coverage threshold of ≤2 reads is applied to identify CpG sites that are insufficiently represented by the different WGBS library methods (based on down-sampled data). In TruSeq DNA Methylation libraries, low coverage sites are mostly found in intergenic regions and introns. The SPLAT and Accel-NGS Methyl-Seq data displayed overall lower number of CpG sites with low coverage, although the number of poorly represented sites in CpG islands and promoter regions are higher compared to the TruSeq DNA methylation libraries.

The greatest total number of CpG sites covered is obtained by the SPLAT dataset followed by the Accel-NGS dataset (see Table 11 of FIG. 28). Moreover, these two protocols provided a better overall genome-wide coverage of CpG sites in repetitive elements, intergenic regions and introns, which are the regions that provide the most important advantage of the WGBS approach over the other targeted methods.

WGBS of human samples are still costly to perform and thus the choice of sample preparation method that will generate the largest amount usable data is important. One must consider: (i) DNA input amount requirements; (ii) whether certain genomic regions/features are of particular interest; (iii) cost efficiency; and (iv) whether the WGBS data will also be used to assess genetic variation and/or copy number alterations, among others. An overall summary of the method evaluation can be found in Table 13 of FIG. 31. The 'post-bisulphite' WGBS library preparation methods bring about a significant reduction in the required DNA input and performed better than the traditional method in all of the metrics presented herein, thus providing a more economical alternative for WGBS especially for scarce samples. In this study, the DNA input amount is set to 100 ng in order to obtain high quality methylation profiles for comparison. However, for the SPLAT and Accel-NGS Methyl-Seq methods the amount of DNA input can be substantially decreased considering that for 100 ng of input DNA, as few as four amplification cycles gave sufficient yield and that the PCR duplication rates are very low. The TruSeq DNA Methylation protocol on the other hand required more than twice as many amplification cycles for the same input amount to obtain the same yield, and thus rather high PCR duplication rates limit the flexibility with respect to input quantity.

One important aspect in choosing a WGBS method is bias in the regions of the genome covered. The SPLAT and Accel-NGS Methyl-Seq methods would be the best if data from the largest number of CpG sites with most even coverage over the genome is desired, especially if genetic variation (for example SNPs) will also be assessed from the WGBS data. In both SPLAT and Accel-NGS Methyl-Seq data, some degree of coverage decline was found in CpG islands and in very GC rich promoter regions, which is a common characteristic of many types WGBS data (Supplementary Figure S8).

Notably, the library preparation cost for SPLAT (<10 $/sample) is less than one tenth of the cost for any of the commercial WGBS methods, making SPLAT a particularly attractive method also for bisulphite sequencing of smaller genomes such as *Arabidopsis* and for applications such as ChIP-bisulphite sequencing (ChIP-BS-seq) (43,44) where the cost of library preparation per sample approaches the cost of sequencing. The post bisulphite adapter tagging (PBAT) method, which is the only other alternative protocol for post bisulphite WGBS library preparation that has been described in a peer-reviewed journal, has the advantage of producing amplification free libraries from low amounts of DNA. However, chimeric reads formed by joining of two distinct genomic regions in PBAT libraries often result in a low mapping efficiency (see online article; https://sequencing.qcfail.com/articles/pbat-libraries-may-generate-chimaeric-read-pairs). In contrast, our results suggest that chimeric reads is an issue that occurs using the original PBAT protocol and not in the methods described here. The mapping procedure used herein does not consider chimeric read pairs as valid alignments. Hence, the high mapping efficiencies for SPLAT as well as the other two post bisulphite methods (>70%) demonstrate that the contribution of chimeric fragments to the mapping efficiency estimation in these libraries is minor.

The TruSeq DNA Methylation method exhibited the best overall coverage of CpG dense regions, such as promoters and CpG islands, however this method suffered from lower coverage of total CpG sites and more data discarded than the other methods. Thus if CpG dense regions are of particular interest, this would be the WGBS method of choice. Lastly, the conventional NEBNextUltra libraries required more input DNA, displayed poor coverage of CpG islands and promoter regions, and generally interrogated fewer CpG sites compared to the other methods and thus this method did not outperform any of the 'post-bisulphite' methods.

The exact cause and origin of the method specific biases are still unclear and multiple mechanisms may be involved. Differences in the efficiency of PCR amplification due to the sequence context and composition of the PCR buffer are recognized sources of coverage bias: DNA polymerases can differ in their ability to efficiently amplify regions of extreme base composition. Hence the AT skewed coverage of the NEBNextUltra libraries in this study might be attributed to the use of the KAPA HiFi Uracil+ polymerase. On the contrary, the same polymerase is used to amplify SPLAT libraries that did not display a similar type of AT bias. Apart from PCR amplification, other causes of coverage bias might be related to specific steps in the different protocols. For instance, non-random bisulphite-induced fragmentation in CpG dense regions might account for increased coverage of GC rich regions in the TruSeq DNA methylation libraries, by increasing the fraction of such regions available for efficient adapter tagging. By contrast, biased fragmentation of GC rich regions in the pre-sheared DNA used for SPLAT and Accel-NGS protocols might lead to very short fragments that are lost in the library preparation. Moreover, secondary structure of single stranded GC rich regions might negatively affect ligation or 3'-end tagging and contribute to the lower representation of such regions in SPLAT and Accel-NGS Methyl-Seq protocols.

The performance of WGBS methods may vary between labs and until a cross-laboratory comparison can be performed any recommendations based on data produced by one lab only should be treated with caution. owever, the characteristics of the different library preparation methods are highly reproducible across the two different cell types analysed. It is chosen to benchmark the methods using the large human genome, an approach that is highly relevant for many researchers, although extensive benchmarking of a large number of samples and methods may be prohibited by the sequencing costs. However, by complementing our benchmarking with publicly available human WGBS data sets from several external laboratories, the same type of coverage biases are observed in the generated data and in the public data (see FIG. 17).

In summary, all 'post bisulphite' library preparation methods perform better than the conventional library preparation method. Concordance of methylation levels across the different methods are high, both at the level of individual CpG sites and across regions. Since no method is completely free from sequence bias, the method of choice depends on the aim of the study and the scientific questions asked. As will be evident to persons having ordinary skill in the art, the inventive method described hereinoffers a straightforward and highly cost efficient approach for WGBS with results which compare favourably to existing methods.

Experimental Protocol. Oligos: (Standard Desalted)

Materials:

Adapter ss1 oligos

5'-GACGTGTGCTCTTCCGATCTNNNNNN-3' Amino Modifier (IDT) (ss1-A) (SEQ ID NO: 1)

5'Phos-AGATCGGAAGAGCACACGTC (ss1-B) (SEQ ID NO: 2)

Adapter ss2 oligos

5'-ACACGACGCTCTTCCGATCT (ss2-A) (SEQ ID NO: 3)

5'-NNNNNNAGATCGGAAGAGCGTCGTGT (ss2-B) (SEQ ID NO: 4)

PCR oligos: universal and index oligos (25 µM stock)

5'-AATGATACGGCGACCACCGAGATCTACACTCTTTCCCTACACGACGCTCTTCCGATCT-3' (PCR Universal primer), (SEQ ID NO: 5)

5'-CAAGCAGAAGACGGCATACGAGATXXXXXXGTGACTGGAGTTCAGACGTGTGCTCTTCCGATCT-3' (PCR Index primer), (SEQ ID NO: 6)

Adapter Annealing:
100 pmol/µl final (of each oligo)=100 µM
1 µl NaCl (5M)
1 µl 20×TE buffer
H$_2$O up to 50 ul
Heat to 95° C. and stepwise decrease temperature to 4-10° C.

Shearing and bisulfite conversion:
Shear DNA to 300-400 bp (Covaris).
Bisulfite conversion with the Zymo EZ DNA Methylation-Gold Kit and elute in 10 µl.
PNK treatment (15 µl total volume)
10 µl DNA
1 µl T4 ligase buffer (30 U/µl Thermo Fisher Scientific)
3.5 µl nuclease free H$_2$O
0.5 µl PNK (10 U/µl Thermo Fisher Scientific)
37° C. for 15 minutes, 95° C. for 3-5 minutes and then place directly on ice/water bath until cool (~5 min) and proceed directly to the next step.
Ligation 1 (30 µl total volume)
Add (in the following order):
15 µl DNA mix
3 µl adapter ss1
5 µl nuclease free H$_2$O
3 µl 10×T4 ligase buffer (Thermo Fisher Scientific)
3 µl PEG4000 (10× solution Thermo Fisher Scientific)
1 µl T4 ligase (30 U/µl Thermo Fisher Scientific)
Spin down briefly and incubate in thermocycler, 20° C. for 1 hr
Clean up with 60 µl AMPure beads and elute in 10 µl nuclease free H2O. SAFE STOP (−20° C.)
Ligation 2 (20 µl total volume)
Denature for 3-5 min at 95° C. and then place directly on ice/water bath until cool (~5 min)
Add (in the following order):
10 µl purified DNA from previous step
2 µl adapter ss2
3 µl H$_2$O
2 µl 10×T4 ligase buffer (Thermo Fisher Scientific)
2 µl PEG4000 (10× solution Thermo Fisher Scientific)
1 µl T4 DNA ligase (30 U/µl Thermo Fisher Scientific)
Spin down briefly and incubate in thermocycler, 20° C. for 1 hr
Clean up with 50 µl AMPure beads and elute in 10 µl H2O. SAFE STOP (−20° C.)
PCR
1 ligated DNA
25 µl 2×KAPA HiFi Uracil+ MasterMix
1 µl universal oligo (25 µM stock conc)
1 µl index oligo (25 µM stock conc)
13 µl H$_2$O
95° C., 3 min
98° C., 15 s
60° C., 30 s
72° C., 2 min
4-5 cycles
72° C., 5 min
Clean up with 1:1 AMPure beads and elute in 20 µl H$_2$O or 10 mM Tris buffer. A small peak at ~60 bp corresponding to residual oligos may be observed if only one bead purification is performed after PCR.

Although no disturbance in sequencing has been observed due to this, however a second bead purification may be performed to remove the majority of the residual oligos if desired. If a second bead purification is performed, elute the DNA from the 1st purification in 50 µl (water or 10 mM Tris buffer) and do a final cleanup with 1:1 AMPure beads. Elute in 20 µl H2O or 10 mM Tris buffer.

Reagents/Supplies Required:
Covaris microtubes
Zymo EZ DNA Methylation Gold kit
T4 DNA ligase HC 30 U/ul (Thermo Fisher Scientific)
PEG4000 (10× solution included with T4 DNA ligase from Thermo Fisher Scientific)
PNK (10 U/µ ThermoFisher Scientific)
KAPA HiFi Uracil+ PCR 2× Master Mix (KAPA Biosystems)
AMPure XP beads (BeckmanCoulter)
80% ethanol
Nuclease free water This protocol is validated by NGS using 100 ng DNA as the input amount and the KAPA HiFi Uracil+ enzyme (4-5 PCR cycles). The method could be performed using other PCR polymerases. Yields from 4-8 nM (with 100 ng input DNA, 4 PCR cycles, final volume 20 µl) are routinely observed, when using high quality gDNA from cell lines. With gDNA samples from primary cells/tissue, which may be of lower quality, yields could be lower.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patents, patent applications, or other documents cited in this application are incorporated by reference in their entirety for all purposes to the same extent as if each individual publication, patent, patent application, or other document are individually indicated to be incorporated by reference for all purposes.

All documents, patents, journal articles and other materials cited in the present application are hereby incorporated by reference.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

In addition, the purpose of the Abstract of the Disclosure in this application is to enable the U.S. Patent and Trademark Office, as well as the public generally, including any scientists, engineers and practitioners in the art who may not be familiar with patent or other legal terms or phraseology to determine the what the technical disclosure of the application describes. Accordingly, while the Abstract of the Disclosure may be used to provide enablement for the following claims, it is not intended to be limiting as to the scope of those claims in any way.

Finally, it is the applicants' intent that only claims which include the express language "means for" or "step for" be interpreted under 35 U.S.C. § 112, paragraph 6. Accordingly, claims that do not expressly include the phrase "means for" or "step for" are not to be interpreted as being within the purview of 35 U.S.C. § 112, paragraph 6, or to be construed as being subject to any case law interpreting the meaning of these phrases.

REFERENCES

The following references are referred to above by number in parentheses and are incorporated herein by reference:

1. Jones, P. A. (2012) Functions of DNA methylation: islands, start sites, gene bodies and beyond. *Nat. Rev. Genet.*, 13, 484-492.
2. Portela, A. and Esteller, M. (2010) Epigenetic modifications and human disease. *Nat. Biotechnol.*, 28, 1057-1068.
3. Frommer, M., McDonald, L. E., Millar, D. S., Collis, C. M., Watt, F., Grigg, G. W., Molloy, P. L. and Paul, C. L. (1992) A genomic sequencing protocol that yields a positive display of 5-methylcytosine residues in individual DNA strands. *Proc. Natl. Acad. Sci. U.S.A.*, 89, 1827-1831.
4. Lister, R., O'Malley, R. C., Tonti-Filippini, J., Gregory, B. D., Berry, C. C., Millar, A. H. and Ecker, J. R. (2008) Highly integrated single-base resolution maps of the epigenome in *Arabidopsis. Cell*, 133, 523-536.
5. Cokus, S. J., Feng, S., Zhang, X., Chen, Z., Merriman, B., Haudenschild, C. D., Pradhan, S., Nelson, S. F., Pellegrini, M. and Jacobsen, S. E. (2008) Shotgun bisulphite sequencing of the *Arabidopsis* genome reveals DNA methylation patterning. *Nature*, 452, 215-219.
6. Bibikova, M., Barnes, B., Tsan, C., Ho, V., Klotzle, B., Le, J. M., Delano, D., Zhang, L., Schroth, G. P., Gunderson, K. L. et al. (2011) High density DNA methylation array with single CpG site resolution. *Genomics*, 98, 288-295.
7. Moran, S., Arribas, C. and Esteller, M. (2015) Validation of a DNA methylation microarray for 850,000 CpG sites of the human genome enriched in enhancer sequences. *Epigenomics*, 8, 389-399.
8. Sandoval, J., Heyn, H., Moran, S., Serra-Musach, J., Pujana, M. A., Bibikova, M. and Esteller, M. (2011) Validation of a DNA methylation microarray for 450,000 CpG sites in the human genome. *Epigenetics*, 6, 692-702.
9. Gu, H., Smith, Z. D., Bock, C., Boyle, P., Gnirke, A. and Meissner, A. (2011) Preparation of reduced representation bisulfite sequencing libraries for genome-scale DNA methylation profiling. *Nature Protocols*, 6, 468-481.
10. Meissner, A., Mikkelsen, T. S., Gu, H., Wernig, M., Hanna, J., Sivachenko, A., Zhang, X., Bernstein, B. E., Nusbaum, C., Jaffe, D. B. et al. (2008) Genome-scale DNA methylation maps of pluripotent and differentiated cells. *Nature*, 454, 766-770.
11. Smith, Z. D., Gu, H., Bock, C., Gnirke, A. and Meissner, A. (2009) High-throughput bisulfite sequencing in mammalian genomes. *Methods* (San Diego, Calif.), 48, 226-232.
12. Boyle, P., Clement, K., Gu, H., Smith, Z. D., Ziller, M., Fostel, J. L., Holmes, L., Meldrim, J., Kelley, F., Gnirke, A. et al. (2012) Gel-free multiplexed reduced representation bisulfite sequencing for large-scale DNA methylation profiling. *Genome Biol.*, 13, R92.
13. Deng, J., Shoemaker, R., Xie, B., Gore, A., LeProust, E. M., Antosiewicz-Bourget, J., Egli, D., Maherali, N., Park, I. H., Yu, J. et al. (2009) Targeted bisulfite sequencing reveals changes in DNAmethylation associated with nuclear reprogramming. *Nat. Biotechnol.*, 27, 353-360.
14. Diep, D., Plongthongkum, N., Gore, A., Fung, H. L., Shoemaker, R. and Zhang, K. (2012) Library-free methylation sequencing with bisulfite padlock probes. *Nat. Methods*, 9, 270-272.
15. Ivanov, M., Kals, M., Kacevska, M., Metspalu, A., Ingelman-Sundberg, M. and Milani, L. (2013) In-solution hybrid capture of bisulfite-converted DNA for targeted bisulfite sequencing of 174 ADME genes. *Nucleic Acids Res.*, 41, e72.
16. Lee, E. J., Pei, L., Srivastava, G., Joshi, T., Kushwaha, G., Choi, J. H., Robertson, K. D., Wang, X., Colbourne, J. K., Zhang, L. et al. (2011) Targeted bisulfite sequencing by solution hybrid selection and massively parallel sequencing. *Nucleic Acids Res.*, 39, e127.
17. Allum, F., Shao, X., Guenard, F., Simon, M. M., Busche, S., Caron, M., Lambourne, J., Lessard, J., Tandre, K., Hedman, A. K. et al. (2015) Characterization of functional methylomes by next-generation capture sequencing identifies novel disease-associated variants. *Nat. Commun.*, 6, 7211.
18. Adey, A. and Shendure, J. (2012) Ultra-low-input, tagmentation-based whole-genome bisulfite sequencing. *Genome Res.*, 22, 1139-1143.
19. Miura, F., Enomoto, Y., Dairiki, R. and Ito, T. (2012) Amplification-free whole-genome bisulfite sequencing by post-bisulfite adapter tagging. *Nucleic Acids Res.* 40, e136.
20. Miura, F. and Ito, T. (2015) Highly sensitive targeted methylome sequencing by post-bisulfite adapter tagging. *DNA Res.*, 22, 13-18.
21. Smallwood, S. A., Lee, H. J., Angermueller, C., Krueger, F., Saadeh, H., Peat, J., Andrews, S. R., Stegle, O., Reik, W. and Kelsey, G. (2014) Single-cell genome-wide bisulfite sequencing for assessing epigenetic heterogeneity. *Nat. Methods*, 11, 817-820.
22. Rosenfeld, C., Goutner, A., Venuat, A. M., Choquet, C., Pico, J. L., Dore, J. F., Liabeuf, A., Durandy, A., Desgrange, C. and De The, G. (1977) An effect human leukaemic cell line: Reh. *Eur. J. Cancer*, 13, 377-379.
23. Krueger, F. and Andrews, S. R. (2011) Bioinformatics (Oxford, England). Vol. 27, pp. 1571-1572.
24. Garcia-Alcalde, F., Okonechnikov, K., Carbonell, J., Cruz, L. M., Gotz, S., Tarazona, S., Dopazo, J., Meyer, T. F. and Conesa, A. (2012) Qualimap: evaluating next- 25. Quinlan, A. R. (2014) BEDTools: the Swiss-Army Tool for genome feature analysis. Curr. Protoc. *Bioinformatics*, 47, doi:10.1002/0471250953.bi1112 s47.
26. Burger, L., Gaidatzis, D., Schubeler, D. and Stadler, M. B. (2013) Identification of active regulatory regions from DNA methylation data. *Nucleic Acids Res.*, 41, e155.
27. Lawrence, M., Huber, W., Pages, H., Aboyoun, P., Carlson, M., Gentleman, R., Morgan, M. T. and Carey, V. J. (2013) Software for computing and annotating genomic ranges. *PLoS Comput. Biol.*, 9, e1003118.
28. Nordlund, J., Backlin, C. L., Wahlberg, P., Busche, S., Berglund, E. C., Eloranta, M. L., Flaegstad, T., Forestier, E., Frost, B. M., Harila-Saari, A. et al. (2013) Genome-wide signatures of differential DNA methylation in pediatric acute lymphoblastic leukemia. *Genome Biol.*, 14, r105.
29. Moore, M. J. and Query, C. C. (2000) Joining of RNAs by splinted ligation. Methods *Enzymol.*, 317, 109-123.
30. Court, F., Tayama, C., Romanelli, V., Martin-Trujillo, A., Iglesias-Platas, I., Okamura, K., Sugahara, N., Simon, C., Moore, H., Harness, J. V. et al. (2014) Genome-wide parent-of-origin DNA methylation analysis reveals the intricacies of human imprinting and suggests a germline methylation-independent mechanism of establishment. *Genome Res.*, 24, 554-569.
31. Uribe-Lewis, S., Woodfine, K., Stojic, L. and Murrell, A. (2011) Molecular mechanisms of genomic imprinting and clinical implications for cancer. *Expert Rev. Mol. Med.*, 13, e2.
32. Benjamini, Y. and Speed, T. P. (2012) Summarizing and correcting the GC content bias in high-throughput sequencing. *Nucleic Acids Res.*, 40, e72.
33. Aird, D., Ross, M. G., Chen, W. S., Danielsson, M., Fennell, T., Russ, C., Jaffe, D. B., Nusbaum, C. and Gnirke, A. (2011) Analyzing and minimizing PCR amplification bias in Illumina sequencing libraries. *Genome Biol.*, 12, R18.

What is claimed is:

1. A method comprising the following steps:
   (a) forming a single stranded treated DNA by treating a double stranded DNA with bisulfite, wherein the bisulfite denatures the double strand DNA and converts non-methylated cytosines in the double stranded DNA into uracils and leaves methylated cytosines in the double stranded DNA unchanged;
   (b) ligating a first adapter to a 3' end of the single stranded treated DNA, thereby forming a once adapter ligated nucleic acid strand, the first adapter comprising a double stranded nucleic acid comprising a top strand and a bottom strand and having a first single-stranded protruding random sequence that is at least 3 bases long and is located at the 3' end of the bottom strand, the first single-stranded protruding random sequence of the first adapter being modified at a 3' end of the bottom strand to prevent self-ligation of the first adapter, and acting as a splint to join the single stranded treated DNA with the first adapter, wherein, in the once adapter ligated nucleic acid strand, a 5' end of the top strand of the first adapter is ligated to the 3' end of the single stranded treated DNA and the first single-stranded protruding random sequence hybridizes with the single stranded treated DNA;
   (c) ligating a second adapter to a 5' end of the once adapter ligated nucleic acid strand, thereby forming a twice ligated nucleic acid strand, the second adapter comprising a double stranded nucleic acid comprising a top strand and a bottom strand and having a second single-stranded protruding random sequence that is at least 3 bases long and is located at the 5' end of the bottom strand, the second single-stranded protruding random sequence acting as a splint to join the once adapter ligated nucleic acid strand with the second adapter, wherein, in the twice ligated nucleic acid strand, a 3' end of the top strand of the second adapter is ligated to the 5' end of the once adapter ligated nucleic acid strand and the second single-stranded protruding random sequence hybridizes with the once adapter ligated nucleic acid strand; and (d) performing a polymerase chain reaction (PCR) on the twice ligated nucleic acid strand, thereby generating copies of the twice ligated nucleic acid strand.

2. The method of claim 1, wherein the double-stranded DNA is a sheared double-stranded DNA from a longer double-stranded DNA.

3. The method of claim 2, further comprising the step of shearing the longer double-stranded DNA.

4. The method of claim 1, wherein the first protruding random sequence of step (b) and the second protruding random sequence of step (c) are 3 to 20 bases long.

5. A method comprising the following steps:
(a) providing a RNA;
(b) ligating a first adapter to a 3' end of the RNA, thereby forming a once adapter ligated nucleic acid strand, the first adapter comprising a double stranded nucleic acid comprising a top strand and a bottom strand and having a first single-stranded protruding random sequence that is at least 3 bases long and is located at the 3' end of the bottom strand, the first single-stranded protruding random sequence of the first adapter being modified at a 3' end of the bottom strand to prevent self-ligation of the first adapter, and acting as a splint to join the RNA with the first adapter, wherein, in the once adapter ligated nucleic acid strand, a 5' end of the top strand of the first adapter is ligated to the 3' end of the RNA and the first single-stranded protruding random sequence hybridizes with the RNA;
(c) ligating a second adapter to a 5' end of the once adapter ligated nucleic acid strand, thereby forming a twice ligated nucleic acid strand, the second adapter comprising a double stranded nucleic acid comprising a top strand and a bottom strand and having a second single-stranded protruding random sequence that is at least 3 bases long and is located at the 5' end of the bottom strand, the second single-stranded protruding random sequence acting as a splint to join the once adapter ligated nucleic acid strand with the second adapter, wherein, in the twice ligated nucleic acid strand, a 3' end of the top strand of the second adapter is ligated to the 5' end of the once adapter ligated nucleic acid strand and the second single-stranded protruding random sequence hybridizes with the once adapter ligated nucleic acid strand; and (d) performing an amplification reaction on the twice ligated nucleic acid strand, thereby generating copies of the twice ligated nucleic acid strand.

6. A method comprising the following steps:
(a) forming a single stranded treated DNA by treating a single stranded DNA with bisulfite, wherein the bisulfite converts non-methylated cytosines in the single stranded DNA into uracils and leaves methylated cytosines in the single stranded DNA unchanged;
(b) ligating a first adapter to a 3' end of the single stranded treated DNA, thereby forming a once adapter ligated nucleic acid strand, the first adapter comprising a double stranded nucleic acid comprising a top strand and a bottom strand and having a first single-stranded protruding random sequence that is at least 3 bases long and is located at the 3' end of the bottom strand, the first single-stranded protruding random sequence of the first adapter being modified at a 3' end of the bottom strand to prevent self-ligation of the first adapter, and acting as a splint to join the single stranded treated DNA with the first adapter, wherein, in the once adapter ligated nucleic acid strand, a 5' end of the top strand of the first adapter is ligated to the 3' end of the single stranded treated DNA and the first single-stranded protruding random sequence hybridizes with the single stranded treated DNA;
(c) ligating a second adapter to a 5' end of the once adapter ligated nucleic acid strand, thereby forming a twice ligated nucleic acid strand, the second adapter comprising a double stranded nucleic acid comprising a top strand and a bottom strand and having a second single-stranded protruding random sequence that is at least 3 bases long and is located at the 5' end of the bottom strand, the second single-stranded protruding random sequence acting as a splint to join the once adapter ligated nucleic acid strand with the second adapter, wherein, in the twice ligated nucleic acid strand, a 3' end of the top strand of the second adapter is ligated to the 5' end of the once adapter ligated nucleic acid strand and the second single-stranded protruding random sequence hybridizes with the once adapter ligated nucleic acid strand; and
(d) performing a PCR on the twice ligated nucleic acid strand, thereby generating copies of the twice ligated nucleic acid strand.

* * * * *

SEQUENCE LISTING

```
<160> NUMBER OF SEQ ID NOS: 6

<210> SEQ ID NO 1
<211> LENGTH: 26
<212> TYPE: DNA
<213> ORGANISM: Artificial Sequence
<220> FEATURE:
<223> OTHER INFORMATION: First part of a partially single stranded,
      partially double stranded piece of DNA
<220> FEATURE:
<221> NAME/KEY: nnnnnn
<222> LOCATION: (21)..(26)
<223> OTHER INFORMATION: "nnnnnn" indicates a random combination of the
      bases A, C, G, and T and which has a 3'-end amino modification (3'
      Amino Modifier, Integrated DNA Technologies) on residue 26
<220> FEATURE:
<221> NAME/KEY: misc_feature
<222> LOCATION: (21)..(26)
<223> OTHER INFORMATION: n is a, c, g, or t

<400> SEQUENCE: 1
gacgtgtgct cttccgatct nnnnnn                                           26

<210> SEQ ID NO 2
<211> LENGTH: 20
<212> TYPE: DNA
<213> ORGANISM: Artificial Sequence
<220> FEATURE:
<223> OTHER INFORMATION: Second part of a partially single stranded,
      partially double stranded piece of DNA

<400> SEQUENCE: 2
agatcggaag agcacacgtc                                                  20

<210> SEQ ID NO 3
<211> LENGTH: 20
<212> TYPE: DNA
<213> ORGANISM: Artificial Sequence
<220> FEATURE:
<223> OTHER INFORMATION: First part of a partially single stranded,
      partially double stranded piece of DNA

<400> SEQUENCE: 3
acacgacgct cttccgatct                                                  20

<210> SEQ ID NO 4
```

```
<211> LENGTH: 26
<212> TYPE: DNA
<213> ORGANISM: Artificial Sequence
<220> FEATURE:
<223> OTHER INFORMATION: Second part of a partially single stranded,
      partially double stranded piece of DNA
<220> FEATURE:
<221> NAME/KEY: nnnnnn
<222> LOCATION: (1)..(6)
<223> OTHER INFORMATION: "nnnnnn" indicates a random combination of the
      bases A, C, G, and T
<220> FEATURE:
<221> NAME/KEY: misc_feature
<222> LOCATION: (1)..(6)
<223> OTHER INFORMATION: n is a, c, g, or t

<400> SEQUENCE: 4
nnnnnnagat cggaagagcg tcgtgt                                          26

<210> SEQ ID NO 5
<211> LENGTH: 58
<212> TYPE: DNA
<213> ORGANISM: Artificial Sequence
<220> FEATURE:
<223> OTHER INFORMATION: PCR Universal primer

<400> SEQUENCE: 5
aatgatacgg cgaccaccga gatctacact ctttccctac acgacgctct tccgatct      58

<210> SEQ ID NO 6
<211> LENGTH: 64
<212> TYPE: DNA
<213> ORGANISM: Artificial Sequence
<220> FEATURE:
<223> OTHER INFORMATION: PCR Index primer
<220> FEATURE:
<221> NAME/KEY: nnnnnn
<222> LOCATION: (25)..(30)
<223> OTHER INFORMATION: "nnnnnn" denotes an Illumina index bar code
      sequence involving a combination of the bases A, C, G, and T.
<220> FEATURE:
<221> NAME/KEY: misc_feature
<222> LOCATION: (25)..(30)
<223> OTHER INFORMATION: n is a, c, g, or t

<400> SEQUENCE: 6
caagcagaag acggcatacg agatnnnnnn gtgactggag ttcagacgtg tgctcttccg    60
atct                                                                 64
```